US012616703B2

(12) United States Patent
Boolell

(10) Patent No.: US 12,616,703 B2
(45) Date of Patent: May 5, 2026

(54) METHODS OF CONTRACEPTION USING NOMEGESTROL ACETATE AND ESTRADIOL

(71) Applicant: THERAMEX HQ UK LIMITED, Belgravia (GB)

(72) Inventor: Mitra Boolell, Belgravia (GB)

(73) Assignee: THERAMEX HQ UK LIMITED, London (GB)

( * ) Notice: Subject to any disclaimer, the term of this patent is extended or adjusted under 35 U.S.C. 154(b) by 393 days.

(21) Appl. No.: 18/031,749

(22) PCT Filed: Oct. 12, 2021

(86) PCT No.: PCT/IB2021/059354

§ 371 (c)(1),
(2) Date: Apr. 13, 2023

(87) PCT Pub. No.: WO2021/229558

PCT Pub. Date: Nov. 18, 2021

(65) Prior Publication Data

US 2023/0390306 A1 Dec. 7, 2023

(30) Foreign Application Priority Data

Oct. 16, 2020 (GB) ..................................... 2016428
Apr. 15, 2021 (GB) ..................................... 2105398
Apr. 15, 2021 (GB) ..................................... 2105401

(51) Int. Cl.

| | |
|---|---|
| ***A61K 31/573*** | (2006.01) |
| ***A61K 9/00*** | (2006.01) |
| ***A61K 31/565*** | (2006.01) |
| ***A61K 31/567*** | (2006.01) |
| ***A61K 31/57*** | (2006.01) |
| ***A61P 7/02*** | (2006.01) |
| ***A61P 15/18*** | (2006.01) |

(52) U.S. Cl.

CPC .......... *A61K 31/573* (2013.01); *A61K 9/0053* (2013.01); *A61K 31/565* (2013.01); *A61K 31/567* (2013.01); *A61K 31/57* (2013.01); *A61P 7/02* (2018.01); *A61P 15/18* (2018.01)

(58) Field of Classification Search

CPC .................................................... A61K 31/573
See application file for complete search history.

(56) References Cited

U.S. PATENT DOCUMENTS 6,906,049 B1 6/2005 Paris et al.

FOREIGN PATENT DOCUMENTS

WO WO 2008/116873 A1 10/2008

OTHER PUBLICATIONS

Lete inaki et al., Eur. J'nal of Contraception and Reproductive Health Care (2015) vol. 20(5).*
Agren Ulla M et al. Eur. J'nal of Contraception and Reproductive Health Care (2011), vol. 16(6).*
Christin-Mattre Sophie et al. (Womens's Health (2013), vol. 9(1).*
Gaussem Pascale et al. (Thrombosis and haemostasis (2011), vol. 105(3).*
European Search Report for European Patent Application No. 24173450.8, mailed Sep. 25, 2024.
European Search Report for European Patent Application No. 24173453.2, mailed Sep. 25, 2024.
Favaloro et al., "Aging hemostasis: changes to laboratory markers of hemostasis as we age—a narrative review", Semin. Thromb. Hemost., Sep. 2014, 40(6): 621-633. Epub Aug. 6, 2014.
Sandset et al., "Mechanisms of thrombosis related to hormone therapy", Thromb. Res., 2009, 123(Suppl 2): S70-S73.
Ågren et al., "Effects of a monophasic combined oral contraceptive containing nomegestrol acetate and 17[beta]-oestradiol compared with one containing levonorgestrel and ethinylestradiol on haemostasis, lipids and carbohydrate metabolism", The European Journal of Contraception and Reproductive Health Care, Dec. 1, 2011, 16(6): 444-457.
Anonymous, "Package leaflet: Information for the user—Zoely 2.5 mg/1.5 mg film-coated tablets", Jun. 1, 2020.
Christin-Maitre et al., "A New Contraceptive Pill Containing 17[beta]-Estradiol and Nomegestrol Acetate", Jan. 1, 2013 (Jan. 1, 2013), vol. 9, No. 1, p. 13-23.
ClinicalTrials.gov ID NCT01650168, "Prospective Controlled Cohort Study on the Safety of a Monophasic Oral Contraceptive Containing Nomegestrol Aceta estradiol (1.5mg) (PRO-E2)", Oct. 6, 2020.
Gaussem et al., "Haemostatic effects of a new combined oral contraceptive, nomegestrol acetate/17[beta]-estradiol, compared with those of levonorgestrel/ethinyl estradiol: A double-blind, randomised study", New Technologies, Diagnostic Tools and Drugs, Jan. 1, 2011, 105(03): 560-567.
International Preliminary Report on Patentability for PCT International Patent Application No. PCT/IB2021/059353, dated Jan. 18, 2023.
International Search Report and Written Opinion for PCT International Patent Application No. PCT/IB2021/059353, dated Jan. 18, 2022.
International Search Report and Written Opinion for PCT International Patent Application No. PCT/IB2021/059354, dated Jan. 18, 2022.
Lete et al., "Haemostatic and metabolic impact of estradiol pills and drospirenone-containing ethinylestradiol pills vs. levonorgestrel-containing ethinylestradiol pills: A literature review", European Journal of Contraception and Reproductive Health Care, Sep. 3, 2015, 20(5): p. 329-343.

(Continued)

*Primary Examiner* — Paul V Ward
(74) *Attorney, Agent, or Firm* — LATHROP GPM LLP; James H. Velema, Esq.; Judith L. Stone-Hulslander

(57) ABSTRACT

Provided are methods of contraception using as a first line combined oral contraceptive (COC), a COC composition comprising nomegestrol acetate (NOMAC) and estradiol or an ester thereof. Said COC compositions are associated with a lower risk of venous thromboembolism (VTE) as compared to other CHCs. The compositions may also be used in methods of treatment in women having conditions linked to menstruation and/or fertility.

19 Claims, 7 Drawing Sheets

(56) References Cited

OTHER PUBLICATIONS

Reis et al., "Progesterone receptor ligands for the treatment of endometriosis: the mechanisms behind therapeutic success and failure", Hum Reprod Update, Jun. 18, 2020, 26(4): 565-585.

Weisberg et al., "Potentially effective therapy of heavy menstrual bleeding with an oestradiol-nomegestrol acetate oral contraceptive: a pilot study", Pilot and Feasibility Studies, Dec. 1, 2017, 3(18): 1-7.

Yildiz, "Approach to the Patient: Contraception in Women With Polycystic Ovary Syndrome", Journ Clin Endocrinol Metab., Mar. 1, 2015, 100(3): 794-802.

U.S. Appl. No. 18/031,748 2023/0398127, filed Apr. 13, 2023 Dec. 14, 2023, Mitra Boolell, Use of Combined Oral Contraceptives Containing Nomegestrol Acetate and Estradiol.

Witjes et al., "Comparative analysis of the effects of nomegestrol acetate/17 β-estradiol and drospirenone/ethinylestradiol on premenstrual and menstrual symptoms and dysmenorrhea", Eur J Contracept Reprod Health Care, Feb. 25, 2015, 20(4): 296-307.

Akintomide et al., "Nomegestrol acetate/17-beta estradiol: a review of efficacy, safety, and patient acceptability", Open Access Journal of Contraception, May 26, 2015, 6: 77-86.

Australian Government, Department of Health and Aging, Australian Public Assessment Report for Nomegestrol acetate/oestradiol, Proprietary Product Name: Zoely, Therapeutic Goods Administration Health Safety Regulation, Oct. 2011.

* cited by examiner

METHODS OF CONTRACEPTION USING NOMEGESTROL ACETATE AND ESTRADIOL

RELATED APPLICATIONS

The instant application is a 35 U.S.C. § 371 filing of International Patent Application No. PCT/IB2021/059354, filed Oct. 12, 2021, which claims priority to Great Britain Patent Application Nos. 2105398.8, filed Apr. 15, 2021, 2105401.0, filed Apr. 15, 2021, and 2016428.1, filed Oct. 16, 2020, the entire contents of which are incorporated herein by reference for all purposes.

FIELD OF THE INVENTION

The present invention relates to methods of contraception comprising at least the step of selecting a combined oral contraceptive (COC) composition comprising nomegestrol acetate (NOMAC) and estradiol or an ester thereof as a first line combined oral contraceptive. Said compositions are associated with a lower risk of venous thromboembolism (VTE) as compared to other CHCs. The compositions may also be used in methods of treatment in women having conditions linked to menstruation and/or fertility.

BACKGROUND TO THE INVENTION

Combined hormonal contraceptives (CHCs), are used to control the menstrual cycle of women by the use of a variety of different means such as transdermal patches, vaginal rings and oral contraceptives. CHC use in women typically prevents ovulation, and is thus a means to prevent pregnancy. One type of CHC known as combined oral contraceptives (COCs) are a popular form of birth control taken by over 100 million women worldwide. CHCs are also used in a clinical setting to treat a range of disorders or conditions linked to menstruation and fertility. Examples include the reduction of heavy menstrual bleeding, regulation of the menstrual cycle, alleviation of dysmenorrhea, treatment of polycystic ovary syndrome, treatment of hirsutism and treatment of premenstrual syndrome (Carey and Allen, *The Obstetrician & Gynaecologist* 2012; 14:223-228).

CHCs (e.g. COCs) typically include an estrogen and a progestogen. A variety of different combinations of estrogens and progestogens are used in different CHCs. Examples of different progestogens used in CHCs currently on the market are levonorgestrel, norethisterone, desogestrel, gestodene, cyproterone acetate, drospirenone, dienogest and nomegestrol acetate. Examples of different estrogens used in CHCs currently on the market are ethinylestradiol, mestranol, estradiol valerate and estradiol.

A significant problem associated with the use of CHCs is increased risk of venous thromboembolism (VTE); VTE is one of the most serious adverse events (AEs) associated with CHC use (World Health Organisation Collaborative Study of Cardiovascular Disease and Steroid Hormone Contraception, *The Lancet*. (1995) 346: 1575-82; Practice Committee of the American Society for Reproductive Medicine, *Fertility and Sterility*. (2016) 107(1): 43-51; Dragoman et al., *Int. J. Gynaecol Obstet*. (2018) 141(3): 287-294; see also: https://www.ema.europa.eu/en/human-regulatory/post-authorisation/referral-procedures/combined-hormonal-contraceptives).

VTE is characterised by a series of events whereby a blood clot or "thrombus" forms in a vein, a portion of the clot breaks away and is carried in the circulation to a distal site where it lodges and causes a blockage in a blood vessel. A pulmonary embolism describes blockage in one of the pulmonary arteries in the lungs caused by a blood clot that has travelled from a vein at a distal site, typically a deep vein of the legs.

In view of the VTE risks associated with CHCs (e.g. COCs) in general, it is important that CHCs having the lowest associated risk of VTE are used as first line CHCs. That is, for women who have not previously used a CHC or for whom there has been a significant hiatus in their use of CHCs, it is important that the first CHC regimen they receive is associated with the lowest risk of VTE.

To date, only a small number of CHCs associated with the lowest risk of VTE are available, thus limiting patient and physician choice. There is therefore a need to identify further CHC compositions associated with the lowest risk of VTE, such that the choice of first line CHC contraception is increased.

SUMMARY OF INVENTION

One example of a CHC already in clinical use is "NOMAC-E2", a COC marketed by Theramex HQ UK Limited as ZOELY®. NOMAC-E2 is a monophasic oral contraceptive containing a fixed dose of nomegestrol acetate (2.5 mg) and 17β-estradiol (1.5 mg). NOMAC-E2 pills are typically taken by women for 24 days followed by 4 days of placebo.

The progestogen contained in NOMAC-E2, nomegestrol acetate or "NOMAC", is a derivative of 19-norprogesterone and is thus structurally very similar to the naturally-occurring progesterone produced by the human body. It has a strong affinity for the progesterone receptor and has strong anti-gonadotropic activity and progesterone receptor-mediated anti-estrogenic activity. It also has moderate anti-androgenic activity, and is devoid of estrogenic, androgenic, glucocorticoid or mineralocorticoid activity.

The estrogen contained in NOMAC-E2 is 17β-estradiol or "E2". E2 is a synthetically produced estrogen but is identical to the natural estrogen-17β-estradiol-produced by the human body; it is classified as a "bio-identical" hormone.

NOMAC-E2 has been in clinical use for some time without any serious health concerns. However, the present application reveals, for the first time, the opportunity to use COCs containing NOMAC and estradiol as a first line contraceptive.

The present application reports the results of a study in which NOMAC-E2 was found to have a low risk of VTE when tested alongside comparator COCs. The comparator COCs included those containing the synthetic progesterone levonorgestrel (LNG). Products containing levonorgestrel are considered in the art to be one of the CHC products associated with the lowest risk of VTE, as are CHC products containing norgestimate and norethisterone. As a result of having the lowest risk of VTE associated with their use, CHC products (e.g. COC products) containing levonorgestrel, norgestimate or norethisterone are currently considered as "first line" contraceptives.

The present application reveals, for the first time, that the use of COCs containing NOMAC and estradiol is associated with a lower risk of VTE relative to COCs currently used as first line contraceptives. These data demonstrate, for the first time, that COCs containing NOMAC and estradiol are suitable for use as a first line combined hormonal contraceptive (CHC).

Accordingly, in a first aspect, the invention provides a method of contraception, comprising:

(i) identifying a woman desirous of contraception as suitable for receiving a combined hormonal contraceptive (CHC);

(ii) selecting a CHC, wherein the selected CHC has been identified as a CHC associated with lowest risk of VTE, wherein the selected CHC is a combined oral contraceptive (COC) composition comprising nomegestrol acetate and estradiol or an ester thereof; and (iii) providing the selected CHC associated with lowest risk of VTE for administration to the woman desirous of contraception.

In certain preferred embodiments, the methods further comprise step (i-a) between steps (i) and (ii). In such embodiments, the method of contraception comprises:

(i) identifying a woman desirous of contraception as suitable for receiving a combined hormonal contraceptive (CHC);

(i-a) identifying a group of one or more CHCs associated with lowest risk of VTE, wherein the identified group of CHCs associated with lowest risk of VTE comprises: a combined oral contraceptive (COC) composition comprising nomegestrol acetate and estradiol or an ester thereof;

(ii) selecting a CHC from the group of CHCs associated with lowest risk of VTE identified in step (i-a), wherein the selected CHC is the combined oral contraceptive (COC) composition comprising nomegestrol acetate and estradiol or an ester thereof; and (iii) providing the selected CHC associated with lowest risk of VTE for administration to the woman desirous of contraception.

In certain preferred embodiments, the method comprises:

(i) identifying a woman desirous of contraception as suitable for receiving a combined hormonal contraceptive (CHC);

(i-a) identifying a group of CHCs associated with lowest risk of VTE, wherein the identified group of CHCs associated with lowest risk of VTE comprises: a combined oral contraceptive (COC) composition comprising nomegestrol acetate and estradiol or an ester thereof, and one or more of a combined oral contraceptive (COC) composition comprising levonorgestrel, a combined oral contraceptive (COC) composition comprising norgestimate, and a combined oral contraceptive (COC) composition comprising norethisterone;

(ii) selecting a CHC from the group of CHCs associated with lowest risk of VTE identified in step (i-a), wherein the selected CHC is the combined oral contraceptive (COC) composition comprising nomegestrol acetate and estradiol or an ester thereof; and (iii) providing the selected CHC associated with lowest risk of VTE for administration to the woman desirous of contraception.

In a further aspect, the invention provides use of a composition comprising nomegestrol acetate and estradiol or an ester thereof in a method of contraception according to the first aspect of the invention.

The invention also provides a composition for use in a method of treating a disease or condition, the method comprising the steps of:

(i) identifying a woman having the disease or condition to be treated as suitable for receiving a combined hormonal contraceptive (CHC);

(ii) selecting a CHC, wherein the selected CHC has been identified as a CHC associated with lowest risk of VTE, wherein the selected CHC is a combined oral contraceptive (COC) composition comprising nomegestrol acetate and estradiol or an ester thereof; and (iii) providing the selected CHC associated with lowest risk of VTE for administration to the woman to be treated, wherein the disease or condition is selected from: painful menstrual bleeding; heavy and/or prolonged menstrual bleeding; acne; ovarian cysts; polycystic ovary syndrome; premenstrual syndrome; endometriosis; and premenstrual dysphoric disorder.

In preferred embodiments of all aspects of the invention described herein, the combined oral contraceptive (COC) composition comprising nomegestrol acetate and estradiol or an ester thereof comprises nomegestrol acetate and 17β-estradiol.

DETAILED DESCRIPTION

A. Definitions

Figure 1:
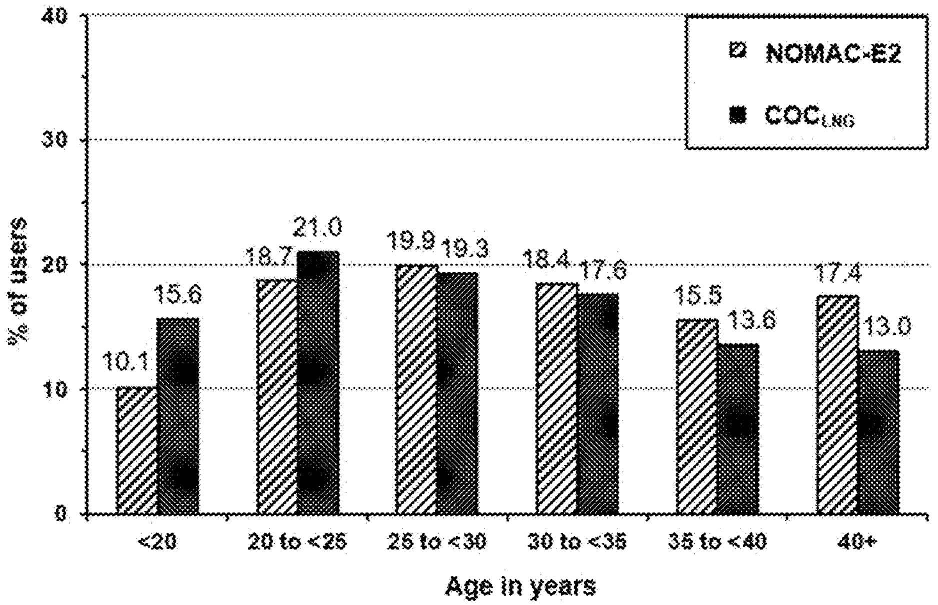
FIG. 1 shows an overview of cohorts included in the clinical study categorised according to age group.

Unless defined otherwise, all technical and scientific terms used herein have the same meaning as is commonly understood by one skilled in the art in the technical field of the invention.

"Combined oral contraceptive" (COC)—as used herein a "combined oral contraceptive" or "COC" refers to a hormonal combination treatment for women that includes an estrogen and a progestogen. Combined oral contraceptives are also referred to in the literature as "combined hormonal contraceptives" or "CHCs". A variety of different combinations of estrogens and progestogens are known to be used in different forms of COCs. The COCs for use according to the present invention comprise nomegestrol acetate (NOMAC) as the progestogen and estradiol or an ester thereof as the estrogen.

"Progestogens"—as used herein the term "progestogens" refers to a class of synthetic steroid hormones which produce similar or equivalent effects to progesterone—the naturally occurring progestogen. Progestogens are also referred to as "gestagens". Progestogens possess antiestrogenic and antigonadotropic properties. Many examples of progestogens are derivatives or metabolites of the naturally-occurring progesterone.

"Nomegestrol acetate"—as used herein "nomegestrol acetate" or "NOMAC" or "NOMAc" refers to a kind of progestogen as represented by the formula:

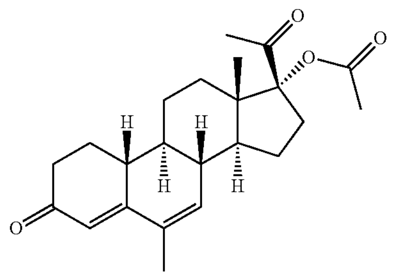

NOMAC is also known as 17α-acetoxy-6-methyl-δ6-19-norprogesterone or as 17α-acetoxy-6-methyl-19-norpregna-4,6-diene-3,20-dione. It is a derivative of progesterone belonging to the 19-norprogesterone and 17α-hydroxyprogesterone groups.

"Estrogens"—as used herein the term "estrogens" (also written as "oestrogens") refers to a class of steroid hormones of which the endogenous or naturally-occurring forms are estrone (E1), estradiol (E2), estriol (E3) and estetrol (E4). Estrogens perform a multitude of functions within the human body including regulation of the menstrual cycle, ovulation and fertility.

"Estradiol"—as used herein the term "estradiol" or "E2" refers to the estrogen as represented by the formula:

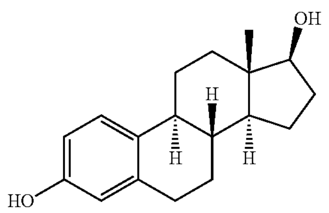

This compound is also known as "17β-estradiol" or "beta-estradiol". Estradiol is the predominant estrogen produced by the human body during a woman's reproductive years.

"Woman of child-bearing age"—as used herein this term refers to a post-pubescent and pre-menopausal woman. A woman of child-bearing age is a woman who is most likely to use the compositions described herein as a means of contraception.

"Means of contraception"—as used herein this term refers to the use of a composition as described herein for the prevention of pregnancy.

"Non-contraceptive use"—as used herein this term refers to the use of a composition as described herein for a purpose other than the prevention of pregnancy.

"Woman identified as at increased risk of VTE"—as used herein this term refers to a woman who is classified as at higher risk of VTE on the basis of having one or more risk factors known to predispose women to VTE.

"Body mass index" (BMI)—as used herein this term refers to the body mass of an individual divided by the square of their body height and is universally expressed in units of $kg/m^2$. According to the World Health Organisation (WHO), an individual with a BMI value of above 30 (>30) is classed as obese. Obesity is a condition in which the excess body fat of an individual has accumulated to such an extent that it can have a negative impact on the health of the individual.

"Plain tablet" as used herein the term "plain tablet" refers to a solid composition that is compressed or otherwise formed into a defined shape and quantity.

"Film-coated tablet"—as used herein the term "film-coated tablet" refers to a tablet encapsulated by a polymer-based coating. The coating may be used to prevent the tablet from degrading in the stomach.

"Sugar-coated tablet"—as used herein the term "sugar-coated tablet" refers to a tablet encapsulated by a mono-, di-, oligo- or poly-saccharide coating. The coating may be used to mask the flavour of particularly unpalatable drugs. The coating can also be used to prevent light or moisture from entering the tablet, which could prevent a drug from breaking down prematurely.

"Soft gelatin capsule"—as used herein the term "soft gelatin capsule" refers to a dosage form in which a liquid or semi-solid centre (inner fill) is encapsulated by a solid capsule (outer shell). The outer shell may comprise, for example, a combination of gelatin, water, opacifier and a plasticizer such as glycerin and/or sorbitol(s).

"Cachets" or "wafer capsules"—as used herein, these terms refer to a seal-shaped capsule or wafer made of flour for enclosing powders of disagreeable taste. The sealed dosage form is wetted and swallowed.

"Pill"—as used herein this term refers to any solid form of medication.

"Powder"—as used herein this term refers to a mixture of solid non-compressed, active drug (e.g. NOMAC-E2) and excipients.

"Excipient"—as used herein this term refers to a compound that is generally safe, non-toxic and neither biologically nor otherwise undesirable. The excipient is substantially inert.

"Oral administration"—as used herein this term means that the dosage form is taken by mouth and is thereby delivered into the gastrointestinal tract.

"Monophasic"—as used herein this term means that a fixed quantity or dosage of the estrogen and/or the progestogen in the COC is administered throughout a treatment cycle. For example, if a treatment cycle consists of 24 daily doses of the COC, a fixed quantity or dosage of the estrogen and/or the progestogen is administered to the woman each day of the 24-day period. The NOMAC-E2 compositions described herein may be administered as monophasic oral contraceptives. For example, a fixed dosage of 2.5 mg and 1.5 mg E2 may be administered daily for a period of 24 days.

"Multiphasic"—as used herein this term means that the quantity or dosage of the estrogen and/or the progestogen varies throughout a treatment cycle. For example, if a treatment cycle consists of daily doses of a COC over a period of several days, the amount of estrogen and/or progestogen administered to the woman on different days of the treatment cycle can vary.

"Acne"—as used herein this term refers to a long-term skin disease that occurs when dead skin cells and oil from the skin clog hair follicles. Typical features of the condition include blackheads or whiteheads, pimples, oily skin, and possible scarring.

"Ovarian cysts"—as used herein this term refers to fluid-filled sacs that develop in or on the ovaries. Typically, an ovarian cyst only causes symptoms if it ruptures, is very large or blocks the blood supply to the ovaries. Symptoms associated with ovarian cysts are pelvic pain, pain during sex, difficulty emptying the bowels, a frequent need to urinate, heavy periods, irregular periods, lighter periods than normal, bloating or a swollen stomach, feeling very full after only eating a little and difficulty getting pregnant.

"Polycystic ovary syndrome" (PCOS)—as used herein this term refers to a condition in which the ovaries contain a large number of follicles. The follicles are underdeveloped sacs in which eggs develop, which means that these sacs are often unable to release an egg. PCOS can result in a lack of ovulation and problems with fertility. Symptoms of PCOS include irregular periods or no periods at all, difficulty getting pregnant, excessive hair growth (hirsutism), (particularly on the face, chest, back or buttocks), weight gain, thinning hair and hair loss from the head, oily skin or acne.

"Premenstrual syndrome" (PMS)—as used herein this term refers to a recurring, cyclical disorder involving behavioural, emotional, social and physical symptoms (Steiner et al., Annu. Rev. Med. (1997) 48:447-455). Symptoms may include, irritability, mood swings, depression, hostility and social withdrawal. Physical symptoms include, bloating, breast tenderness, myalgia, migraines, headaches, or fatigue.

"Endometriosis"—as used herein this term refers to a condition where tissue similar to the lining of the womb starts to grow elsewhere in the reproductive system, such as the ovaries and fallopian tubes. Symptoms may include any one or more of: abdominal pain, back pain, period pain, pain during or after sex, pain during defecation or urination, feeling sick, constipation, diarrhoea, blood in the stool, difficulty getting pregnant, heavy periods or depression.

"Premenstrual dysphoric disorder" (PMDD)—as used herein this term refers to a disorder possessed by a subgroup of women with PMS. PMDD is considered a severe form of PMS. Symptoms can include any one or more of: mood swings, feeling upset or tearful, feeling angry or irritable, feelings of anxiety, feeling hopeless, feelings of tension or being on edge, difficulty concentrating, feeling overwhelmed, lack of energy, less interest in activities normally enjoyed, suicidal feelings, breast tenderness or swelling, pain in your muscles and joints, headaches, feeling bloated, changes in appetite or sleep problems.

"Menstrual cycle regulation"—as used herein this term refers to the regulation of the menstrual cycle using hormonal treatment. Hormonal treatments may be used to regulate the menstrual cycle in women who exhibit problems including but not limited to menstrual cycles of differing length, painful menstruation, very heavy bleeding at menstruation.

"Venous thromboembolism" (VTE)—as used herein the term "venous thromboembolism" or "VTE" is used to describe a series of events in which:

- a blood clot (also known as a thrombus) forms in a vein;
- the blood clot or a fragment thereof dislodges from the original site of formation;
- the blood clot or fragment thereof is transported via the circulatory system to another blood vessel
- the blood clot or fragment thereof lodges in the other blood vessel, thereby causing a partial or total blockage of the blood flow in the affected vessel.

There are a number of risk factors associated with the development of VTE. The use of hormone-based medicines is associated with an increased VTE risk. Hormone-based medicines include, for example, CHCs, oral contraceptives and hormone replacement therapies for women.

"Deep vein thrombosis"—as used herein the term "deep vein thrombosis" or "DVT" is used to describe a thrombus that forms in the deep veins of the legs, groin or arms. Symptoms associated with DVT are pain or tenderness in the arms or legs (typically in the thigh or calf), swollen legs or arms, skin that is red or warm to the touch, red streaks on the skin or a change in colour of the skin.

"Pulmonary embolism"—as used herein the term "pulmonary embolism" or "PE" is used to refer to a blood clot or thrombus that has travelled to the lungs from a distal site in the circulation and is blocking or partially blocking a blood vessel of the lungs. Symptoms associated with PE are a sudden unexplained shortness of breath, rapid breathing, sudden unexplained coughs, sharp chest pain, rapid or irregular heart rate, light-headedness and severe pain in the stomach.

"Placebo"—as used herein refers to a dosage form containing no active ingredient.

B. Methods of Contraception

As discussed herein, the use of CHCs has been connected with an increase in the risk of blood clots in the veins or "venous thromboses" and a concomitant increase in the risk of VTE. For example, whilst about 2 out of 10,000 women who are not using a CHC and are not pregnant develop a blood clot in a vein in a year, women taking CHCs have a 3-3.5 fold increased risk in developing blood clots (FSRH Clinical Guideline: Combined Hormonal Contraception, 2020).

It is also known that certain CHC compositions are associated with a greater risk of blood clots than others and that this may depend on the progestogen type and the estrogen dose contained within the CHCs (FSRH Clinical Guideline: Combined Hormonal Contraception, 2020). By way of example, about 5-7 out of 10,000 women using a CHC containing levonorgestrel, norethisterone or norgestimate develop a blood clot in a vein in a year, whereas this incidence increases to about 6-12 out of 10,000 women using a CHC containing etonogestrel or norelgestromin and about 9-12 out of 10,000 women using a CHC containing drospirenone, gestodene or desogestrel (see https://www.ema.europa.eu/en/human-regulatory/post-authorisation/referral-procedures/combined-hormonal-contraceptives). CHCs containing any one of levonorgestrel, norethisterone and norgestimate are considered as CHCs associated with the lowest incidences of blood clotting and associated with the lowest risk of VTE out of the tested CHCs. This property means that typically CHCs containing levonorgestrel, norethisterone or norgestimate are favoured by clinicians for use as first line contraceptives.

As reported herein, it has unexpectedly been found that women taking a COC containing NOMAC and estradiol exhibit a reduced risk of VTE. This reduction in risk was seen relative to women taking other COCs containing different forms of progestogen and estrogen. Specifically, women taking a COC containing NOMAC and estradiol developed VTE, as measured by a combination of DVT of the lower extremities and PE, at a rate of only 2.0 per 10,000 women years. In contrast, women taking a COC containing levonorgestrel ($COC_{LNG}$) developed VTE, as measured by a combination of DVT of the lower extremities and PE, at a rate of 3.1 per 10,000 women years. Furthermore, women taking other forms of COC containing different estrogens and/or progestogens developed VTE at a rate of 4.8 per 10,000 women years.

As described above, COCs containing levonorgestrel such as $COC_{LNG}$ are considered to be one of the CHCs associated with the lowest risk of VTE (other CHCs associated with the lowest risk of VTE are COCs containing norethisterone or norgestimate). Surprisingly therefore, women taking a COC containing NOMAC and estradiol had a lower risk of VTE than those taking $COC_{LNG}$. These results reveal that a COC containing NOMAC and estradiol is suited for use as a first line contraceptive in addition to those CHCs deemed to have the lowest risk of VTE such as COCs containing levonorgestrel, norethisterone or norgestimate.

Accordingly, in a first aspect provided herein is a method of contraception, comprising the steps of:

(i) identifying a woman desirous of contraception as suitable for receiving a combined hormonal contraceptive (CHC);

(ii) selecting a CHC, wherein the selected CHC has been identified as a CHC associated with lowest risk of VTE, wherein the selected CHC is a combined oral contraceptive (COC) composition comprising nomegestrol acetate and estradiol or an ester thereof; and (iii) providing the selected CHC associated with lowest risk of VTE for administration to the woman desirous of contraception.

In certain preferred embodiments, the method further comprises step (i-a) between steps (i) and (ii), wherein step (i-a) comprises:

(i-a) identifying a group of one or more CHCs associated with lowest risk of VTE, wherein the identified group of CHCs associated with lowest risk of VTE comprises: a combined oral contraceptive (COC) composition comprising nomegestrol acetate and estradiol or an ester thereof;

and wherein the selection in step (ii) is made from the group identified in step (i-a).

In certain preferred embodiments, the method further comprises step (i-a) between steps (i) and (ii), wherein step (i-a) comprises:

(i-a) identifying a group of CHCs associated with lowest risk of VTE, wherein the identified group of CHCs associated with lowest risk of VTE comprises: a combined oral contraceptive (COC) composition comprising nomegestrol acetate and estradiol or an ester thereof, and one or more of a combined oral contraceptive (COC) composition comprising levonorgestrel, a combined oral contraceptive (COC) composition comprising norgestimate, and a combined oral contraceptive (COC) composition comprising norethisterone;

and wherein the selection in step (ii) is made from the group identified in step (i-a).

In certain preferred embodiments, the method further comprises step (i-a) between steps (i) and (ii), wherein step (i-a) comprises:

(i-a) identifying a group of CHCs associated with lowest risk of VTE, wherein the identified group of CHCs associated with lowest risk of VTE comprises: a combined oral contraceptive (COC) composition comprising nomegestrol acetate and estradiol or an ester thereof, a combined oral contraceptive (COC) composition comprising levonorgestrel, a combined oral contraceptive (COC) composition comprising norgestimate, and a combined oral contraceptive (COC) composition comprising norethisterone;

and wherein the selection in step (ii) is made from the group identified in step (i-a).

All embodiments described herein are equally applicable to other aspects of the invention as described, in particular in sections C and D.

(i) Risk of VTE and/or Risk of Unintended Pregnancy

As described herein, a significant decrease in the incidence of VTE was observed in women taking a COC containing NOMAC and estradiol as compared with women taking other forms of COC. The methods of contraception according to the invention require identifying a woman desirous of contraception suitable for receiving a combined hormonal contraceptive (CHC). In some embodiments, in order to identify a woman desirous of contraception as suitable for receiving a CHC, the woman's risk of VTE is determined. For example, in one embodiment, the risk of VTE is determined for the woman in step (i). In another embodiment, the risk of VTE is determined prior to step (i).

As used herein, the "risk of VTE" of the woman refers to the woman's likelihood of developing VTE prior to administration of the COC composition comprising nomegestrol acetate and estradiol or an ester thereof in accordance with the methods of the invention. Whilst there is no single cause of blood clots and/or VTE, numerous factors are known to increase a woman's risk of developing VTE. Exemplary contributory factors include: genetic predisposition to blood clotting, previous incidences of blood clots and/or VTE, increasing age, higher BMI, lifestyle factors and thrombophilia. Therefore, a clinician is able to determine the risk of VTE in a woman or women based on the incidence and severity of known risk factors that each contribute in part to the overall risk of blood clots and/or VTE. These factors are described in further detail elsewhere (see "(iii) Woman desirous of contraception").

Given that CHC use increases the risk of blood clot formation and associated VTE, in some embodiments the woman or women desirous of contraception may have no known risk factors that pre-dispose her or them to blood clots and/or VTE. In one embodiment, the woman is identified as not a woman at increased risk of VTE. In other embodiments, the woman is identified as at increased risk of VTE.

In some embodiments, risk of VTE is determined as an incidence or risk of "idiopathic VTE". Idiopathic VTE is also known as "unprovoked VTE" or "spontaneous VTE". Idiopathic VTE encompasses all forms of VTE that are not associated with temporary risk factors; temporary risk factors include but are not limited to pregnancy, delivery, trauma, immobilization, long-haul travel, surgery and chemotherapy.

In some embodiments, risk of VTE is determined as an incidence or risk of deep vein thrombosis (DVT). In some embodiments, a risk of VTE is determined as an incidence or risk of pulmonary embolism (PE). In some embodiments, a risk of VTE is determined as an incidence or risk or DVT and PE. As described above, DVT and PE are both common occurrences in the chain of events associated with VTE and thus determining the incidence or risk of one or both of these occurrences is directly linked to the risk of VTE.

As demonstrated herein, use of a COC composition comprising nomegestrol acetate and estradiol or an ester thereof results in a significantly lower risk of unintended pregnancy (i.e. becoming pregnant during the period of contraceptive use) compared to other COCs such as $COC_{LNG}$. Accordingly, the methods of contraception in accordance of the invention will be particularly beneficial to women at increased risk of unintended pregnancy. Thus, in some embodiments, the woman desirous of contraception is identified as suitable for receiving a combined hormonal contraceptive (CHC) based on a determination of the unintended pregnancy risk of the woman. In some embodiments of the methods of the invention, the method comprises the step of determining the unintended pregnancy risk of the woman desirous of contraception.

(ii) CHC Associated with Lowest Risk of VTE

First line CHCs such as $COC_{LNG}$ are typically adopted as first line COCs because they are associated with the lowest risk of VTE. As described herein, a significant decrease in the incidence of VTE was observed in women taking a COC containing NOMAC and estradiol as compared with women taking first line COCs typically associated with lowest risk of VTE, such as $COC_{LNG}$. The results presented herein therefore reveal for the first time that a COC composition comprising nomegestrol acetate and estradiol or an ester thereof has a VTE risk lower than current first line COC compositions. The present application is thus the first disclosure that a COC composition comprising nomegestrol acetate and estradiol or an ester thereof can be a first line combined oral contraceptive—i.e. a COC that is a CHC associated with the lowest risk of VTE.

Therefore the method of contraception in accordance with the invention comprises selecting the combined oral contraceptive (COC) composition comprising nomegestrol acetate and estradiol or an ester thereof as a CHC associated with lowest risk of VTE.

The methods of contraception in accordance with the invention are aimed at providing a CHC associated with the lowest risk of VTE to a woman desirous of contraception, where that CHC is in the form of a COC. In certain embodiments, the CHC is selected from a group of CHCs that have been identified as CHCs associated with lowest risk of VTE. In an embodiment, the CHC associated with lowest risk of VTE is selected from the group comprising: a combined oral contraceptive (COC) composition comprising nomegestrol acetate and estradiol or an ester thereof. In a further embodiment, the CHC associated with lowest risk of VTE is selected from the group comprising a combined oral contraceptive (COC) composition comprising nomegestrol acetate and estradiol or an ester thereof, and a combined oral contraceptive (COC) composition comprising levonorgestrel. In an embodiment, the CHC associated with lowest risk of VTE is selected from the group comprising: a combined oral contraceptive (COC) composition comprising nomegestrol acetate and estradiol or an ester thereof, a combined oral contraceptive (COC) composition comprising levonorgestrel and a combined oral contraceptive (COC) composition comprising norgestimate. In a further embodiment, the CHC associated with lowest risk of VTE is selected from the group comprising a combined oral contraceptive (COC) composition comprising nomegestrol acetate and estradiol or an ester thereof, and one or more of a combined oral contraceptive (COC) composition comprising norgestimate. In another embodiment, the CHC associated with lowest risk of VTE is selected from the group comprising a combined oral contraceptive (COC) composition comprising nomegestrol acetate and estradiol or an ester thereof, and a combined oral contraceptive (COC) composition comprising norethisterone. In certain embodiments, the group of CHCs that have been identified as CHCs associated with lowest risk of VTE comprises: a combined oral contraceptive (COC) comprising nomegestrol acetate and estradiol or an ester thereof; a combined oral contraceptive (COC) comprising levonorgestrel; a combined oral contraceptive (COC) comprising norgestimate; and a combined oral contraceptive (COC) comprising norethisterone.

Alternatively or in addition, the CHC is selected from a group of CHCs associated with lowest risk of VTE, the group comprising: a COC composition comprising nomegestrol acetate and estradiol or an ester thereof, and a COC composition comprising levonorgestrel, norethisterone, desogestrel, gestodene, cyproterone acetate, drospirenone, or dienogest.

In some embodiments, the COC composition comprising levonorgestrel, the COC composition comprising norgestimate or COC composition comprising norethisterone further comprises a synthetic estrogen. The synthetic estrogen may be selected from the group including but not limited to ethinylestradiol, or mestranol. In certain embodiments the synthetic estrogen is ethinylestradiol.

In some embodiments, the COC composition containing levonorgestrel further comprises ethinylestradiol.

In some embodiments, COC containing levonorgestrel is monophasic. In some embodiments, the monophasic COC contains levonorgestrel and 20-30 mcg ethinylestradiol. In some embodiments, the monophasic COC contains levonorgestrel and 20 mcg ethinylestradiol. In some embodiments, the COC containing levonorgestrel is multiphasic. In other embodiments, the multiphasic COC contains levonorgestrel and 40 mcg ethinylestradiol. The dose of levonorgestrel in the COC may be in the range from 100 mcg to 250 mcg. In certain embodiments, the dose of levonorgestrel in the COC is 150 mcg.

Women administered a COC composition comprising nomegestrol acetate and estradiol or an ester thereof in accordance with the invention will benefit from a reduced risk of VTE compared to the risk associated with use of other COCs. In some embodiments, the risk of VTE is at least 10%, at least 20%, at least 25%, at least 30%, at least 40% lower in a woman or women administered nomegestrol acetate and estradiol or an ester thereof in accordance with the invention, as compared with the risk associated with other COCs used by women.

For example, in some embodiments, the risk of VTE is lowered by at least 20% in women administered compositions comprising NOMAC and estradiol or an ester thereof as compared with women taking $COC_{LNG}$. In some embodiments, the risk of VTE is lowered by at least 25% in women administered compositions comprising NOMAC and estradiol or an ester thereof as compared with women taking $COC_{LNG}$. In some embodiments, the risk of VTE is lowered by at least 30% in women administered compositions comprising NOMAC and estradiol or an ester thereof as compared with women taking $COC_{LNG}$. In some embodiments, the risk of VTE is lowered by at least 35% in women administered compositions comprising NOMAC and estradiol or an ester thereof as compared with women taking $COC_{LNG}$.

In preferred embodiments, the risk of VTE is lowered by at least 40% in women administered compositions comprising NOMAC and estradiol or an ester thereof as compared with women taking $COC_{LNG}$. In further preferred embodiments, the risk of VTE is lowered by 50% or halved in women administered compositions comprising NOMAC and estradiol or an ester thereof as compared with women taking $COC_{LNG}$.

(iii) Woman Desirous of Contraception

The methods of contraception in accordance with the invention are generally applicable to any woman or women desirous of contraception.

In some embodiments, the woman or women desirous of contraception is/are of child-bearing age. Accordingly, in some embodiments, the compositions are administered to a woman or women aged 12-55. In some embodiments, the woman or women is/are aged 15-55. In some embodiments, the woman or women is/are aged 15-50. In some embodiments, the woman or women is/are aged 15-45.

In some embodiments, the woman or women is/are 35 years of age or above; optionally 36 years of age or above; optionally 37 years of age or above; optionally 38 years of age or above; optionally 39 years of age or above; optionally 40 years of age or above.

In an alternative embodiment, the woman or women is/are less than 35 years of age. For example, the woman or women is/are 15, 16, 17, 18, 19, 20, 21, 22, 23, 24, 25, 26, 27, 28, 29, 30, 31, 32, 33 or 34 years of age.

As demonstrated herein, administration of COC compositions comprising NOMAC and estradiol or an ester thereof significantly reduces the risk of unintended pregnancy during the period of contraceptive use compared to other COCs such as $COC_{LNG}$. In certain embodiments, the woman desirous of contraception is at risk of unintended pregnancy—i.e. of becoming pregnant during a period of contraceptive use. In certain preferred such embodiments, the woman is less than 35 years of age.

The method of contraception according to the invention is especially beneficial to a woman or women who may be at increased risk of VTE. In some embodiments, the increased risk of VTE is associated with COC use.

Certain groups of women are also known to be at increased risk of developing VTE per se as compared with the general population or with the risk seen in women generally. Accordingly, in certain embodiments, the woman or women desirous of contraception is/are classified as at increased risk of VTE. A woman or women classified as "at increased risk of VTE" may have an increased risk of VTE that is independent of the elevated VTE risk associated with COC use.

In some embodiments, the woman or women desirous of contraception is an overweight woman or are overweight women. In some embodiments, the woman or women desirous of contraception is/are obese. In some embodiments, the woman or women desirous of contraception has/have a body mass index (BMI) of >23 kg/m$^2$. In some embodiments, the woman or women desirous of contraception has/have a BMI of >25 kg/m$^2$. In some embodiments, the woman or women desirous of contraception has/have a BMI≤30 kg/m$^2$. In other embodiments, the woman or women desirous of contraception has/have a BMI >30 kg/m$^2$ In some embodiments, the woman or women desirous of contraception has/have a BMI >35 kg/m$^2$. In some embodiments, the woman or women desirous of contraception has/have a BMI >40 kg/m$^2$. In some embodiments, the woman or women desirous of contraception has/have a BMI of 30 kg/m$^2$ to 35 kg/m$^2$.

In some embodiments the woman or women desirous of contraception is/are categorised as overweight or obese according to one or measures used in clinical practice.

In some embodiments, the woman or women desirous of contraception has/have hypertension or who has/have a history of hypertension (for example during pregnancy).

In some embodiments, the woman or women desirous of contraception is/are smokers.

In some embodiments, the woman or women desirous of contraception has/have diabetes.

In some embodiments, a woman or women desirous of contraception has or have a condition selected from: cancer; systemic lupus erythematosus (SLE); haemolytic uraemic syndrome; chronic inflammatory bowel disease (such as Crohn's disease or ulcerative colitis); and sickle cell disease. In alternative embodiments, a woman or women desirous of contraception does not have any condition in the list consisting of: cancer; systemic lupus erythematosus (SLE); haemolytic uraemic syndrome; chronic inflammatory bowel disease (such as Crohn's disease or ulcerative colitis); and sickle cell disease.

In one embodiment, a woman or women desirous of contraception has or have cancer. The cancer may be selected from breast cancer or cervical cancer. In an alternative embodiment, a woman or women desirous of contraception does not have cancer.

In some embodiments, a woman or women desirous of contraception is or are postpartum. The risk of VTE is significantly increased in pregnant and postpartum women. For example, incidence rates typically rise to 5-20/10,000 women years in pregnancy and 40-65/10,000 women years postpartum (see Practice Committee of the American Society for Reproductive Medicine, *Fertility and Sterility*. (2016) 107(1): 43-51). In some embodiments, the woman or women desirous of contraception is or are breastfeeding 6 weeks to 6 months postpartum. In some embodiments, the woman or women desirous of contraception is or are not breastfeeding 3 weeks to 6 weeks postpartum.

In certain embodiments, a woman or women desirous of contraception has or have a family history of VTE (especially VTE in a parent or sibling). Alternatively or in addition, a woman or women desirous of contraception have an acquired predisposition for VTE, for example by virtue of having a condition that affects blood clotting. Non-limiting examples of conditions that affect blood clotting are protein C deficiency, antithrombin III deficiency, Factor V Leiden thrombophilia and antiphospholipid syndrome (APS).

In further embodiments, a woman or women desirous of contraception has or have undergone major surgery. This could include but is not limited to surgery to the legs or pelvis, neurosurgery, or major trauma.

In further embodiments, a woman or women desirous of contraception exhibit(s) long-term immobility, for example by virtue of wheelchair use.

In further embodiments, a woman or women desirous of contraception who have had one or more previous occurrences of deep vein thrombosis (DVT) and/or pulmonary embolism (PE).

In other words, the woman or women may have a clinical history that is indicative of an increased risk of VTE.

In some embodiments, a woman or women desirous of contraception has or have a plurality of risk factors associated with increased risk of developing VTE.

In certain alternative embodiments, the woman desirous of contraception is identified as suitable for receiving a combined hormonal contraceptive (CHC) if the woman is identified as not a woman at increased risk of VTE.

The methods of contraception according to the invention are for a woman or women desirous of contraception. In one embodiment, the woman or women has/have not previously been administered a CHC. For example, the woman or women may not have taken any contraceptives or may not have required any contraceptives. In another embodiment, the woman or women has/have not previously been administered a COC. For example, the woman may have previously received a non-oral form of contraceptive.

In alternative embodiments, the woman has previously been administered a COC in their lifetime. Such women may be classified as "restarters". In one embodiment, the woman may not have been administered a COC for at least 4 weeks. In further embodiments, the woman may not have been administered a COC for at least 1 week, at least 2 weeks, at least 3 weeks, at least 5 weeks, at least 6 weeks, at least 7 weeks or at least 8 weeks. In further embodiments the woman may not have been administered a COC for at least 2 months. In further embodiments the woman may not have been administered a COC for 3 months or more, 4 months or more, 5 months or more, 6 months or more or, 12 months or more.

In other embodiments, the woman has previously been administered a CHC in their lifetime. In one embodiment, the woman may not have been administered a CHC (e.g. a COC) for at least 2 months or more, 3 months or more, 4 months or more, 5 months or more, 6 months or more or, 12 months or more.

In certain embodiments, the woman desirous of contraception is administered the selected CHC of lowest VTE risk solely for the purposes of contraception.

As reported herein, the risk of VTE, as measured by DVT of the lower extremities and PE, can be particularly high in women restarting COC treatment—see Table 7, which reports an incidence of 5.0 per 10,000 WY in women restarting $COC_{LNG}$ use as compared with an incidence of 3 per 10,000 WY for the total population of women receiving $COC_{LNG}$. Significantly, this increase in VTE risk was not seen in restarters administered NOMAC-E2—an incidence of 2.4 per 10,000 WY was observed in women restarting NOMAC-E2 as compared with an incidence of 2 per 10,000 WY for the total population of women receiving NOMAC-E2. This indicates that the compositions comprising nomegestrol acetate and estradiol or an ester thereof as described herein are particularly beneficial for a woman who has previously received COCs or CHCs.

(iv) Compositions Comprising NOMAC and Estradiol or an Ester Thereof

The COC compositions described herein for use in the methods in accordance with the invention comprise NOMAC and estradiol or an ester thereof. The compositions are thus themselves COCs wherein the progestogen active ingredient is NOMAC and the estrogen active ingredient is estradiol or an ester thereof.

In some embodiments, the NOMAC and estradiol or ester thereof are present in a weight ratio of 5 to 0.5. In some embodiments, the NOMAC and estradiol or ester thereof are present in a weight ratio of 3 to 1. In a preferred embodiment, the NOMAC and estradiol or ester thereof are present in a weight ratio of 1.67 to 1.

In some embodiments, the NOMAC is present in an amount ranging from 1.5 mg to 3.75 mg. In some embodiments, the estradiol or ester thereof is present in an amount ranging from 0.5 mg to 3 mg. In some embodiments, the NOMAC is present in an amount of about 2.5 mg and the estradiol or ester thereof is present in an amount of about 1.5 mg.

In a preferred embodiment, the NOMAC is present in an amount of 2.5 mg and the estradiol or ester thereof is present in an amount of 1.5 mg.

In some embodiments, the compositions for use comprise NOMAC in combination with an estradiol ester. Such estradiol esters include but are not limited to estradiol valerate, estradiol benzoate, estradiol phenylpropionate, estradiol enanthate, estradiol acetate, estradiol cypionate, estradiol dipropionate, estradiol undecylate and polyestradiol phosphate (an estradiol ester in polymeric form).

In preferred embodiments, the composition comprises NOMAC in combination with 17β-estradiol (also referred to herein as E2). In a particularly preferred embodiment, the 17β-estradiol is in hemihydrate form. In preferred embodiments, the composition comprises 2.5 mg NOMAC and 1.5 mg 17β-estradiol.

Without wishing to be bound by theory, it is thought that compositions comprising NOMAC and 17β-estradiol might be beneficial as a first line contraceptive since the progestogen and estrogen ingredients present in these compositions are structurally very similar (in the case of NOMAC) and identical (in the case of 17β-estradiol) to the naturally-occurring forms of these hormones found in women.

The compositions that are used in the methods according to the invention may be formulated so as to comprise one or more pharmaceutically acceptable carriers or excipients. Alternatively or in addition, the compositions for use according to the invention may be formulated as to comprise one or more additional agents selected from but not limited to: binding agents; disintegrants; lubricants; glidants; fillers; and/or diluents.

In some embodiments, the composition comprises one or more additional agents selected from: lactose monohydrate; anhydrous lactose; spray-dried lactose; sifted/sieved/milled lactose; crystalline lactose; sucrose; trehalose; dextrose; fructose; dextrates; dextrin; dextrose anhydrous; sorbitol; mannitol; xylitol; maltitol solution; glucose liquid; and polydextrose.

Alternatively or in addition, the composition may comprise one or more additional agents selected from: microcrystalline cellulose; cellulose powder or derivatives thereof with different molecular weights including other forms such as gel, gum, crystal, cotton, sugar, alpha-grade, paste, guar gum; pre-gelatinised maize starch; croscarmellose sodium; alginic acid; acacia; calcium phosphate (dibasic anhydrous/dihydrate, tribasic); carboxymethylcellulose sodium; carrageenan; silicified microcrystalline cellulose; cellulose acetate; cellulose acetate phthalate; carbomer; hydroxypropyl cellulose (or low substituted); hydroxypropyl starch; hypromellose (and acetate succinate and phthalate); hydroxyethyl cellulose; hydroxyethylmethyl cellulose; hydroxypropyl cellulose; sodium phosphate (dibasic or monobasic); sodium starch glycolate; maize starch; sucralose; povidone; polyoxyethylen (including alkly ethers, castor oil derivatives, sorbitan fatty acid esters, stearate, glycerides); shellac; sodium alginate; vitamin E polyethylene glycol succinate; calcium sulfate; carbomer (polyacrylic acid, carboxyvinyl polymer, carbopol); carrageenan; chitosan; hydroxypropyl starch; corn starch; pregelatinized starch; dextrates; dextrin; dextrose; glycerol behenate; Novagel®/Avicel® (such as PH 101, 102, 301, 302); Vivapur®; Emcocel®; Comprecel®; and Microcel®.

Alternatively or in addition, the composition may comprise one or more additional agents selected from: crospovidone; PVP; polyvinyl N-pyrrolidone; povidone, plasdon; polypasdone (including its XL/XL-10/INF-10) with differing particle size distribution (standard, fine, superfine, micronized); guar gum; hydroxypropyl betadex; hydroxypropyl starch; sodium starch glycolate; Kollidon® (with full range of K value-PVP K12, PVP K15, PVP K17, PVP K30, PVP K60, PVP K90, bulk density, hydration capacity, and peroxide levels); and croscarmellose sodium.

Alternatively or in addition, the composition may comprise one or more additional agents selected from: talc; magnesium silicate (monoclinic or triclinic); aluminium magnesium silicate; talcum; corn starch; kaolin; saponite; montmorillonite; and titanium dioxide.

Alternatively or in addition, the composition may comprise one or more additional agents selected from: magnesium stearate (generally a mixture of crystalline forms-anhydrate, monohydrate, dihydrate and trihydrate with Mg, Ca, Na); stearic acid; a composition consisting of magnesium stearate to palmitate, and other fatty acid esters, such as palmitic acid, myristic acid, glyceride esters (glyceryl monostearate, glyceryl tribehenate, glyceryl dibehenate or Compritol 888) and sugar esters (sorbitan monostearate and sucrose monopalmitate); sodium stearyl fumarate; hydrogenated vegetable oil; hydrogenated castor oil; sterotex; talc; waxes (such as anionic emulsifying, carnauba, cetyl esters, microcrystalline, nonionic emulsifying, white or yellow); Stear-O-Wet; boric acid; carbowax (PEG) 4000/6000; sodium oleate; sodium benzoate; sodium acetate; sodium lauryl sulfate; and Mg-lauryl sulfate Alternatively or in addition, the composition may comprise one or more additional agents selected from: colloidal anhydrous silica or silicon dioxide colloidal; Aerosil; Cab-O-Sil; fumed silica; anhydrous silicic acid; silicic anhydride; silicon dioxide fumed; silicon dioxide amorphous; magnesium trisilicate; magnesium silicate; and magnesium aluminium silicate.

In some embodiments, the composition comprises at least one additional agent selected from: lactose monohydrate; microcrystalline cellulose; crospovidone; talc; magnesium stearate; and colloidal anhydrous silica; or any combination thereof.

In some embodiments, the composition comprises the additional agents: lactose monohydrate; microcrystalline cellulose; crospovidone; talc; magnesium stearate; and colloidal anhydrous silica.

In some embodiments, the composition comprises or consists of:

| Constituent | Amount (mg) |
|---|---|
| NOMAC | 1.5-3.5 |
| 17β-estradiol | 0.5-2.5 |
| lactose monohydrate | 15-98 |
| microcrystalline cellulose | 5-90 |
| crospovidone | 1-5 |
| talc | 0.2-2 |
| magnesium stearate | 0.2-2 |
| colloidal anhydrous silica | 0.2-2 |

In preferred embodiments, the composition comprises or consists of:

| Constituent | Amount (mg) |
|---|---|
| NOMAC | 2.5 |
| 17β-estradiol | 1.5 |
| lactose monohydrate | 57.7 |
| microcrystalline cellulose | 14 |
| crospovidone | 2.4 |
| talc | 0.7 |
| magnesium stearate | 0.7 |
| colloidal anhydrous silica | 0.44 |

In preferred embodiments, the composition comprises or consists of:

| Constituent | Amount (mg) |
|---|---|
| NOMAC | 2.5 |
| 17β-estradiol hemihydrate | 1.55* |
| lactose monohydrate | 57.7 |
| microcrystalline cellulose | 14 |
| crospovidone | 2.4 |
| talc | 0.7 |
| magnesium stearate | 0.7 |
| colloidal anhydrous silica | 0.44 |

*Equivalent to 1.5 mg estradiol

In some embodiments, the composition is formulated for oral administration.

In some embodiments, the composition is in the form of plain or film-coated tablets, sugar-coated tablets, soft gelatin capsules, wafer capsules, pills, cachets or powders.

In preferred embodiments, the composition is in the form of a film-coated tablet. In some embodiments, the film-coating comprises one or more of: poly(vinyl alcohol); titanium dioxide; macrogol 3350; and/or talc.

(v) Administration Schedule

The compositions that are used in accordance with the methods of the invention are, in some embodiments, administered at a frequency of once per day i.e. daily. In some embodiments, the compositions are administered daily for a period of between 21 and 28 days. In some embodiments, the compositions are administered daily for a period of between 21 and 28 days per cycle. In some embodiments, the compositions are administered for a period of between 21 and 28 consecutive days per cycle. In other embodiments, the compositions are administered for a period of 21 to 28 days intermittently per cycle. In a preferred embodiment, the compositions are administered once a day for a period of 24 consecutive days per cycle.

The compositions may be administered once a day for a period of 24 consecutive days followed by a hormone-free period of 4 consecutive days. The compositions may administered once a day for a period of 24 consecutive days followed by administration of a placebo tablet once a day for a period of 4 consecutive days. The administration of 24 consecutive daily doses of the composition followed by 4 consecutive daily doses of placebo may constitute one cycle. One cycle may be followed directly by one or more consecutive cycles.

In preferred embodiments, the composition is administered as a monophasic composition for the duration of the period of administration.

(vi) Pharmaceutical Kits

In some embodiments, the compositions that are used in accordance with the methods of the invention, are provided in the form of pharmaceutical kits, optionally wherein the kits contain instructions for use.

A pharmaceutical kit may comprise a plurality of dosage units of compositions as described herein. The pharmaceutical kit may optionally further comprise at least one placebo dosage unit.

In preferred embodiments, the pharmaceutical kits comprise or consist of 24 dosage units of a composition as described herein and 4 dosage units of a placebo.

C. Uses as Methods of Contraception

In another aspect, the invention provides use of a composition comprising NOMAC and estradiol or an ester thereof as a method of contraception in accordance with the methods of the invention.

All embodiments described herein relating to the methods of contraception according to the preceding aspects of the invention (see in particular, Section B) are equally applicable to this further aspect of the invention.

D. Method of Treatment

In a further aspect, the invention provides a composition for use in a method of treating a disease or condition, the method comprising the steps of:

(i) identifying a woman having the disease or condition to be treated as suitable for receiving a combined hormonal contraceptive (CHC);

(ii) selecting a CHC, wherein the selected CHC has been identified as a CHC associated with lowest risk of VTE, wherein the selected CHC is a combined oral contraceptive (COC) composition comprising nomegestrol acetate and estradiol or an ester thereof; and (iii) providing the selected CHC associated with lowest risk of VTE for administration to the woman to be treated, wherein the disease or condition is selected from: painful menstrual bleeding; heavy and/or prolonged menstrual bleeding; acne; ovarian cysts; polycystic ovary syndrome; premenstrual syndrome; endometriosis; and premenstrual dysphoric disorder.

In a further aspect, the invention provides a method of treating a condition selected from: painful menstrual bleeding; heavy and/or prolonged menstrual bleeding; acne; ovarian cysts; polycystic ovary syndrome (PCOS); premenstrual syndrome (PMS); endometriosis; and premenstrual dysphoric disorder (PMDD), wherein the method comprises the steps of:

(i) identifying a woman having the disease or condition to be treated as suitable for receiving a combined hormonal contraceptive (CHC);

(ii) selecting a CHC, wherein the selected CHC has been identified as a CHC associated with lowest risk of VTE, wherein the selected CHC is a combined oral contraceptive (COC) composition comprising nomegestrol acetate and estradiol or an ester thereof; and (iii) providing the selected CHC associated with lowest risk of VTE for administration to the woman to be treated.

In some embodiments, the method comprises step (i-a) between steps (i) and (ii), wherein step (i-a) comprises:

(i-a) identifying a group of CHCs associated with lowest risk of VTE, wherein the identified group of CHCs associated with lowest risk of VTE comprises: a combined oral contraceptive (COC) composition comprising nomegestrol acetate and estradiol or an ester thereof, and one or more of a combined oral contraceptive (COC) composition comprising levonorgestrel, a combined oral contraceptive (COC) composition comprising norgestimate, and a combined oral contraceptive (COC) composition comprising norethisterone; and wherein the selection in step (ii) is made from the group identified in step (i-a).

In some embodiments, the condition is a menstrual disorder. In some embodiments, the condition is painful menstrual bleeding. In some embodiments, the condition is dysmenorrhea. In some embodiments, the condition is heavy and/or prolonged menstrual bleeding. In some embodiments, the condition is metrorrhagia. In some embodiments, the condition is polymenorrhea. In some embodiments, the condition is ovarian cysts. In some embodiments, the condition is polycystic ovary syndrome (PCOS). In some embodiments, the condition is premenstrual syndrome (PMS). In some embodiments, the condition is endometriosis. In some embodiments, the condition is premenstrual dysphoric disorder (PMDD). In some embodiments, the condition is acne. In some embodiments, the condition is hirsutism.

In some embodiments, a composition as described herein is administered to a woman or women so as to prevent or treat one or more, two or more, three or more, four or more, five or more conditions selected from: painful menstrual bleeding; heavy and/or prolonged menstrual bleeding; acne; ovarian cysts; polycystic ovary syndrome (PCOS); premenstrual syndrome (PMS); endometriosis; and premenstrual dysphoric disorder (PMDD).

In some embodiments, the condition is irregular menstrual cycle lengths. The method of treatment as disclosed herein may normalise the duration of the menstrual cycle in a woman or women having irregular menstrual cycle lengths.

Alternatively or in addition, the method of treatment as disclosed herein may be used to normalise the frequency of ovulation in a woman or women having irregular patterns of ovulation.

All embodiments described herein relating to the methods of contraception according to the preceding aspects of the invention according to the preceding aspects of the invention (see in particular, Section B) are equally applicable to these further aspects of the invention.

In certain embodiments of all aspects of the invention, the steps of the method are all performed by the same person.

INCORPORATION BY REFERENCE

Various publications are cited in the foregoing description and throughout the following example, each of which is incorporated by reference herein in its entirety.

EXAMPLE

The invention will be further understood with reference to the following non-limiting example.

Prospective, Controlled Cohort Study on the Safety of a Monophasic Oral Contraceptive Containing Nomegestrol Acetate (2.5 mg) and 17β-Estradiol (1.5 mg) (the PRO-E2 Study)

1. Summary

A large clinical study was conducted to evaluate the safety of a monophasic combined oral contraceptive (COC) containing nomegestrol acetate (NOMAC) and 17β-estradiol. This COC—referred to herein as NOMAC-E2—has been on the market for some time with no serious health concerns. However, this multinational, non-randomized, controlled, prospective, active surveillance study was conducted so to as monitor the risk of rare serious adverse outcomes in a large cohort of women taking NOMAC-E2 as compared with a large cohort of women taking a different COC—referred to herein as $COC_{LNG}$. The $COC_{LNG}$ comparators used in this study are considered to be one of the CHCs associated with the lowest risk of VTE in patients and because of this they are typically used as first line CHCs.

The main clinical outcome of interest was venous thromboembolism (VTE), and specifically deep vein thrombosis (DVT) of the lower extremities and pulmonary embolism (PE).

The results presented herein are based on 91,313 women (44,559 NOMAC-E2 users and 46,754 $COC_{LNG}$ users) recruited between August 2014 and September 2019. Starters (i.e. those women who had not received COC treatment before) comprised 62.6% of NOMAC-E2 users and 64.4% of $COC_{LNG}$ users. A total of 37.4% of NOMAC-E2 users and 35.6% of $COC_{LNG}$ users were restarters (i.e. women who had received COC treatment previously). During the follow-up phase, sub-cohorts formed as women switched to other COCs or stopped hormonal contraceptive use. These sub-cohorts included: $COC_{Other}$ (i.e. users of COCs other than NOMAC-E2 or $COC_{LNG}$), other hormonal contraceptives (OHC) (e.g. users of progestin-only OCs, vaginal rings, intrauterine devices or implants) and Ex-users (i.e. women not using a hormonal contraceptive).

The NOMAC-E2 cohort had a higher mean age than the $COC_{LNG}$ cohort and the difference was statistically significant (NOMAC-E2: 31.0 years; $COC_{LNG}$: 29.3 years). NOMAC-E2 users and $COC_{LNG}$ users had a similar mean weight (NOMAC-E2: 63.3 kg; $COC_{LNG}$: 63.1 kg) and mean BMI (NOMAC-E2: 23.2; $COC_{LNG}$: 23.3). Gynaecological history and baseline risk factors differed little between the cohorts.

Data from 144,901 women years (WY) of observation have been collected, including 48,846 WY from NOMAC-E2 users and 54,037 WY from $COC_{LNG}$ users. The remaining observation time was contributed by the sub-cohorts which formed during follow-up: $COC_{Other}$ (8,300 WY), OHC (2,364 WY) and ex-users (31,354 WY).

Overall, there were 30 deaths: 10 due to accidents (3 in NOMAC-E2 users, 3 in $COC_{LNG}$ users, 1 in an OHC user and 3 in ex-users), 7 due to cancer (2 in NOMAC-E2 users and 5 in ex-users), 5 due to unknown causes (1 in a NOMAC-E2 user, 1 in a $COC_{LNG}$ user and 3 in ex-users), 3 due to infectious diseases (1 in a NOMAC-E2 user, 1 in a $COC_{LNG}$ user and 1 in an ex-user), 2 due to acute myocardial infarctions (AMIs) (1 in a $COC_{LNG}$ user and 1 in a $COC_{Other}$ user), 1 due to a stroke (in an ex-user), 1 due to cerebral edema (in a $COC_{LNG}$ user) and 1 due to accidental poisoning and exposure to noxious substances (in an ex-user). Blinded to the hormonal contraceptive exposure status, an independent Safety Monitoring and Advisory Council (SMAC) assessed that the deaths were unrelated to hormonal contraceptive use (19 deaths), a relationship was unlikely (4 deaths) or possible (3 deaths). Four other deaths (2 $COC_{LNG}$ users and 2 ex-users) were categorized as indeterminate because insufficient information was available to enable the SMAC to reasonably assess a relationship between death and hormonal contraceptive use.

Overall, there were 34 VTEs in the main analysis of the primary outcome (DVT of the lower extremities and PE): 9 NOMAC-E2 (2.0 per 10,000 WY; 95% CI, 0.9-3.7), 15 $COC_{LNG}$ (3.0 per 10,000 WY; 95% CI, 1.7-5.0), 4 $COC_{Other}$ (5.2 per 10,000 WY; 95% CI, 1.4-13.4), 1 OHC (4.8 per 10,000 WY; 95% CI, 0.1-26.8) and 5 ex-users (1.8 per 10,000 WY; 95% CI, 0.6-4.1). The Cox proportional hazards a priori expert model (complete case analysis) resulted in a crude hazard ratio ($HR_{crude}$) for NOMAC-E2 versus $COC_{LNG}$ of 0.65 (95% CI, 0.28-1.48). After adjusting for age, BMI, family history of VTE and current duration of HC use, the adjusted hazard ratio ($HR_{adj}$) was 0.59 (95% CI, 0.25-1.35).

In total, 46 VTEs were included in the analysis of the secondary outcome of all VTE (i.e. not restricted to DVT of the lower extremities and PE): 12 NOMAC-E2 (2.5 per 10,000 WY; 95% CI, 1.3-4.3), 20 $COC_{LNG}$ (3.7 per 10,000 WY; 95% CI, 2.3-5.7), 5 $COC_{Other}$ (6.0 per 10,000 WY; 95% CI, 2.0-14.1), 1 OHC (4.2 per 10,000 WY; 95% CI 0.1-23.5) and 8 ex-users (2.6 per 10,000 WY; 95% CI, 1.1-5.0).

Overall, 35 of the 46 confirmed VTEs were considered idiopathic VTEs. The numbers and incidence rates for each (sub-) cohort were as follows: NOMAC-E2 10 VTEs (2.0 per 10,000 WY; 95% CI, 1.0 3.8), $COC_{LNG}$ 15 VTEs (2.8 per 10,000 WY; 95% CI, 1.6-4.6), $COC_{Other}$ 5 VTEs (6.0 per 10,000 WY; 95% CI, 2.0-14.1), OHC 1 VTE (4.2 per 10,000 WY. 95% CI, 0.1-23.5) and ex-users 4 VTEs (1.3 per 10,000 WY; 95% CI, 0.35-3.3).

There were 16 confirmed ATEs: 4 NOMAC-E2 (0.8 per 10,000 WY; 95% CI, 0.2-2.1), 7 $COC_{LNG}$ (1.3 per 10,000 WY; 95% CI, 0.5-2.7), 1 $COC_{Other}$ (1.2 per 10,000 WY; 95% CI, 0.0-6.7) and 4 ex-users (1.3 per 10,000 WY; 95% CI, 0.35-3.3).

Overall, there were 62 thrombolic events (VTE and ATE): 16 in NOMAC-E2 users (3.3 per 10,000 WY; 95% CI, 1.9-5.3), 27 in $COC_{LNG}$ users (5.0 per 10,000 WY; 95% CI, 3.3-7.3), 6 in $COC_{Other}$ users (7.2 per 10,000 WY; 95% CI, 2.7-15.7), 1 in an OHC user (4.2 per 10,000 WY; 95% CI, 0.1-23.5) and 12 in ex-users (3.8 per 10,000 WY; 95% CI, 2.0-6.7). A Cox regression analysis was performed to compare the risk in NOMAC-E2 users versus $COC_{LNG}$ users. The a priori expert model yielded an $HR_{crude}$ of 0.68 (95% CI, 0.36-1.27) and, after adjusting for age, BMI, current duration of HC use, family history of VTE and family history of ATE, an $HR_{adj}$ of 0.64 (95% CI, 0.34-1.20).

There were 289 unintended pregnancies in hormonal contraceptive users: 64 NOMAC-E2 (0.15 per 100 WY; 95% CI, 0.11-0.19), 200 $COC_{LNG}$ (0.41 per 100 WY; 95% CI, 0.35-0.47), 19 $COC_{Other}$ (0.26 per 100 WY; 95% CI, 0.16-0.40) and 6 OHC (0.28 per 100 WY; 95% CI, 0.10-0.61). Unintended pregnancy was statistically significantly less likely in NOMAC-E2 users compared to $COC_{LNG}$ users ($p<0.0001$).

There were 261 cases of cholelithiasis (18.0 per 10,000 WY; 95% CI, 15.9-20.3): 84 NOMAC-E2 (17.2 per 10,000 WY; 95% CI, 13.7-21.3), 92 $COC_{LNG}$ (17.0 per 10,000 WY; 95% CI, 13.7-20.9), 21 $COC_{Other}$ (25.3 per 10,000 WY; 95% CI, 15.7-38.6), 8 OHC (33.8 per 10,000 WY; 95% CI, 14.6-66.6) and 56 ex-users (17.9 per 10,000 WY; 95% CI, 13.5-23.2) There were 24 cases of inflammatory bowel disease: 4 NOMAC-E2 (0.8 per 10,000 WY; 95% CI, 0.2-2.1), 13 $COC_{LNG}$ (2.4 per 10,000 WY; 95% CI, 1.3-4.1), 3 $COC_{Other}$ (3.6 per 10,000 WY; 95% CI, 0.75-10.6) and 4 ex-users (1.3 per 10,000 WY; 95% CI, 0.35-3.3).

Of the 191 cases of general hepatobiliary disorders, 65 were in NOMAC-E2 users (13.3 per 10,000 WY; 95% CI, 10.3-17.0), 63 in $COC_{LNG}$ users (11.7 per 10,000 WY; 95% CI, 9.0-14.9), 12 in $COC_{Other}$ users (14.5 per 10,000 WY; 95% CI, 7.5-25.2), 6 in OHC users (25.4 per 10,000 WY; 95% CI, 9.3-55.2) and 45 in ex-users (14.4 per 10,000 WY; 95% CI, 10.5-19.2).

There were 188 cases of new depression or worsening of an existing depression: 46 cases in NOMAC-E2 users (9.4 per 10,000 WY; 95% CI, 6.9-12.6), 80 in $COC_{LNG}$ users (14.8 per 10,000 WY; 95% CI, 11.7-18.4), 13 in $COC_{Other}$ users (15.7 per 10,000 WY; 95% CI, 8.3-26.8), 8 in OHC users (33.8 per 10,000 WY; 95% CI, 14.6-66.6) and 41 in ex-users (13.1 per 10,000 WY; 95% CI, 9.4-17.7).

There was a trend for mean body weight to increase modestly between study entry and the follow-up time points for NOMAC-E2 and $COC_{LNG}$ users.

In general, NOMAC-E2 users appeared to experience more of an improvement in their acne during follow-up (in comparison with baseline) than $COC_{LNG}$ users.

Further details of this clinical study are provided below.

2. List of Abbreviations

AE Adverse Event
AMI Acute Myocardial Infarction
AT As Treated
ATE Arterial Thromboembolism
BMI Body Mass Index
COC Combined Oral Contraceptive
$COC_{LNG}$ Levonorgestrel-containing COC
$COC_{LNGMono/20\ mcg}$ Monophasic levonorgestrel-containing COC with 20 mcg ethinylestradiol
$COC_{LNGMono/30\ mcg}$ Monophasic levonorgestrel-containing COC with 30 mcg ethinlyestradiol
$COC_{LNGMulti}$ Multiphasic levonorgestrel-containing COC
$COC_{Other}$ Combined oral contraceptive other than NOMAC-E2 or $COC_{LNG}$
CT Computer Tomography
CVA Cerebrovascular Accidents
DVT Deep Venous Thrombosis
ECG Electrocardiogram
EE Ethinylestradiol
EURAS European Active Surveillance (study)
LNG Levonorgestrel
MRT Magnetic Resonance Tomography
MRI Magnetic Resonance Imaging
NOMAC-E2 Nomegestrol Acetate and Estradiol
HR Hazard ratio
$HR_{adj}$ Hazard ratio (adjusted)
$HR_{crude}$ Hazard ratio (crude)
OC Oral Contraceptive
OHC Other hormonal contraceptive (i.e., progestin-only method, injections, implants, levonorgestrel-releasing intrauterine devices, contraceptive patches)
PE Pulmonary Embolism
PIP Pediatric Investigation Plan
SAE Serious Adverse Event
VTE Venous Thromboembolism
WY Woman-years

3. Rationale and Background

NOMAC-E2 is a monophasic OC containing a fixed dose of nomegestrol acetate (2.5 mg) and 17β-estradiol (1.5 mg), which is taken for 24 days followed by 4 days of placebo. Nomegestrol acetate has a strong affinity for the progesterone receptor and has strong anti-gonadotropic activity and progesterone receptor-mediated anti-estrogenic activity, moderate anti-androgenic activity, and is devoid of estrogenic, androgenic, glucocorticoid or mineralocorticoid activity. The estrogen contained in NOMAC-E2 is 17β-estradiol, an estrogen identical to the endogenous human 17β-estradiol.

Clinical experience with NOMAC-E2 and established COCs suggests that serious clinical outcomes are rare when using NOMAC-E2 and other COCs (including COCs containing levonorgestrel ($COC_{LNG}$)). One of the most serious adverse events (AEs) associated with COC use is VTE. The European Active Surveillance Study (EURAS) comprehensively investigated the risk of VTE and other serious cardiovascular outcomes that might be associated with OC use (see Dinger J C et al., *Contraception.* (2007) 75:344-354). However, similar comprehensive data from large, controlled, prospective studies with defined follow-up procedures of rare SAEs and low loss to follow-up rates have not previously been made available for NOMAC-E2.

Data from randomized clinical trials has not revealed any serious health concerns for NOMAC-E2. However, the statistical power to detect rare adverse events has been limited in these earlier studies. Based on general public concerns about the safety of COCs, the Prospective Controlled Cohort Study on the Safety of a Monophasic Oral Contraceptive containing Nomegestrol Acetate (2.5 mg) and 17β-estradiol (1.5 mg), (PRO-E2) Study focused not only on VTE but also on ATE, depressive disorders, cholelithiasis, general hepatobiliary disorders, inflammatory bowel disease, effects on fertility, pregnancy outcomes, weight change and the effect on acne.

The PRO-E2 study was conducted as a required post-authorization safety study in accordance with Article 10a of the EU Regulation 726/2004. The objective of the PRO-E2 Study was to assess the cardiovascular and other health risks associated with the use of NOMAC-E2 compared with the use of $COC_{LNG}$ during standard clinical practice. The study included women who have been newly prescribed NOMAC-E2 or $COC_{LNG}$ (either as first-ever users or as restarters with a COC intake break of at least 2 months). During the follow-up phase, sub-cohorts formed as women switched to other COCs (forming a $COC_{Other}$ sub-cohort), other hormonal contraceptives such as progestin-only methods, injections, implants, levonorgestrel-releasing intrauterine devices and contraceptive patches (forming an OHC sub-cohort), or stopped hormonal contraceptive use (forming an Ex-user sub-cohort).

As specified in the study protocol dated 5 Feb. 2014, participating countries included Australia, Austria, France, Germany, Hungary, Italy, Poland, Russia and Spain. Subsequent to the approval of the Study Protocol in April 2014, three additional countries (Mexico, Colombia and Sweden) were included in the study (as reflected in the final version of Amendment 1 of the Study Protocol, dated 20 Jun. 2019).

Patient recruitment began in August 2014 in Germany. Thereafter, recruitment began in Australia, Austria, Colombia, France, Hungary, Italy, Mexico, Poland, Russia, Spain and Sweden after country-specific requirements were met.

4. Research Questions and Objectives

The primary objective of the study was to characterize and compare the risks of NOMAC-E2 use with $COC_{LNG}$ use in a study population that is representative of the actual users of the individual preparations.

This included an estimate of the absolute risk of rare serious adverse outcomes.

The main clinical outcomes of interest were VTE, specifically:

DVT of the lower extremities
PE

Secondary objectives of the study were to measure/describe for NOMAC-E2 users and compare to users of $COC_{LNG}$ during standard clinical practice:

All VTE, including thromboses of renal, mesenteric, portal and retinal veins
ATE incidence rate. ATE includes acute myocardial infarction (AMI) and cerebrovascular accidents (CVA)
Depressive disorders incidence rate (based on the assessment of attending physicians who are specialized in psychiatry and the Three Item Mental Health Inventory)
Cholelithiasis incidence rate Inflammatory bowel disease incidence rate Effect on fertility Drug utilization pattern and baseline risk for primary and secondary clinical outcomes-in particular cardiovascular outcomes Pregnancy outcomes Additional secondary objectives were to measure/describe the following factors for NOMAC-E2 users and compare to users of $COC_{LNG}$ during standard clinical practice:

Weight change

General hepatobiliary disorders

Effect on acne

5. Research Methods

Study Design

The study was a large, multinational, controlled, prospective, active surveillance study that followed two cohorts. The cohorts consisted of new users (starters and restarters) of two different groups of hormonal contraceptives: NOMAC-E2 and $COC_{LNG}$. Starters were first-ever users of any COC. Restarters were users who were restarting hormonal contraceptive use with a COC (same COC as before or a new COC) after a break of at least 2 months. This observational study provides standardized, comprehensive, reliable information on these treatments in a routine clinical practice setting.

Study participants were recruited via an international network of COC-prescribing health care professionals (e.g. gynecologists, general practitioners, midwives). After study entry, study participants were followed for a period of 12 to 24 months for rare serious safety outcomes. Regular, active contact with the study participants provided the necessary information on health-related events or changes in health status. Additional follow-up procedures were used to validate self-reported events.

During the follow-up phase, direct contact with the study participants allowed for almost all relevant clinical outcomes to be captured. However, laypersons often misclassified adverse events (e.g., pneumonia as "pulmonary embolism" or migraine attacks as "stroke" even if modern imaging procedures do not provide any indication of the perceived event). This type of inaccuracy in patient reports required careful validation of the reported events. This was accomplished by contacting the relevant physicians (i.e. the treating physicians) and by reviewing source documents. Under routine medical conditions, clinical outcomes were not always confirmed by diagnostic procedures with high specificity. Therefore, reported serious clinical outcomes were classified as "confirmed" or "not confirmed" by the physicians overseeing this study according to a predefined algorithm. At the end of the study, this classification was verified by blinded independent adjudication.

Setting

The PRO-E2 Study was divided into 2 phases: a patient-completed baseline survey, which involved an initial consultation at baseline with a participating physician during routine clinical practice; and a follow-up phase, which included two follow-up contacts with the patient during the first year, and then a follow-up at 24 months after study entry.

Subjects and Study Size, Including Dropouts

The overall recruitment target was 101,000 study participants (50,500 NOMAC-E2 users and 50,500 $COC_{LNG}$ users) recruited by participating physicians. This was planned to provide approximately 150,000 WY, assuming a drop-out rate of approximately 0.7% per month. Subjects were considered for enrolment in the PRO-E2 Study after the participating physician and the woman had determined that NOMAC-E2 or $COC_{LNG}$ use was appropriate. There were no specific medical inclusion/exclusion criteria and no age restrictions (to fulfil the pediatric investigation plan (PIP) requirement in the EU). However, women who 1) have been pregnant within 3 months before treatment initiation or 2) have a history of cancer/chemotherapy or an increased genetic risk for VTE at baseline were excluded from the analysis of VTE.

Once enrolled, a study participant could discontinue (and restart) use of hormonal contraception or could switch to another hormonal contraceptive at any time. However, subjects continued to be followed up regardless of whether they remained on the prescribed contraceptive, provided that they did not withdraw their consent.

Variables

The following variables were recorded at baseline: ID number; date of birth; age at menarche; problems associated with menstrual period (e.g. irregular bleeding/spotting); hormonal contraceptive use (duration, brand name of most recent hormonal contraceptive, hormonal contraceptive use within the past two months); reason(s) for prescription; previous pregnancies; pregnancy within past three months; number of live births; number of miscarriages, stillbirths, abortions; family history of VTE and ATE; mood over the past four weeks; acne; impact of severe acne on self-esteem; medical history (including DVT, PE, myocardial infarction, stroke, thrombophilia or inherited increased risk of blood clots, depression requiring treatment, diseases of the liver, diseases of the gallbladder or biliary tract, inflammatory bowel disease, cancer, diabetes, high blood pressure, other severe diseases, operations); regular use of concomitant medication; height; weight; smoking status and number of cigarettes smoked per day; level of education; date of completion.

During follow-up, the following variables were recorded: ID number; new SAEs/AEs; hospitalization (planned/unplanned, reason, operation performed); hormonal contraceptive use since last contact (stopped/switched/unchanged, reason for stopping/switching); concomitant medication; pregnancy (occurrence, planned/unplanned, length of time to become pregnant, pregnant despite OC use, possible reasons for contraceptive failure); delivery; serious health issues of the newborn; mood over the past four weeks; acne; impact of severe acne on self-esteem; smoking status and number of cigarettes smoked per day; weight; date of completion; change of personal contact details; name of treating physician in case of SAE/AE.

Exposure

Cohort 1: NOMAC-E2

Cohort 2: Levonorgestrel-containing COCs: 1) monophasic preparations containing 20-30 mcg of ethinylestradiol; 2) multiphasic preparations containing up to 40 mcg of ethinylestradiol Outcome The primary endpoint was VTE. Specific VTEs-DVT of the lower extremities and PE-were the primary outcomes of interest. Inferential statistics are based on the VTE HR for NOMAC-E2 vs. $COC_{LNG}$. This study provides data that are sufficiently robust to eliminate a 1.5-fold risk in VTE for NOMAC-E2 compared to $COC_{LNG}$.

The secondary endpoints also investigated are described above in the research questions and objectives section.

Covariates

In relation to VTE risk, the covariates include age, BMI, duration of current use and family history of VTE.

Data Sources and Measurement

Study participants documented on questionnaires their exposure to hormonal contraceptives and concomitant medications, the occurrence of primary and secondary outcomes and the existence of potential confounding factors and potential effect modifiers. If relevant, recruiting and attending physicians provided further information on additional documentation sheets. Follow-up assessments for each study participant were scheduled at 6 months, 12 months and 24 months after study entry. Questionnaires were provided to the participating women. In some cases, events were reported by the participant or by relatives, friends or attending physicians between the regular follow-ups. All reports (independent of the source of information) were validated according to a standardized process The follow-up questionnaires addressed the occurrence of adverse events (in particular, SAEs). If applicable, reasons for COC discontinuation or a switch to another hormonal contraceptive were requested.

Study Procedures

Under routine medical conditions, the diagnosis of an SAE is not always confirmed by a diagnostic method with high specificity. Therefore, SAEs were classified as "confirmed" or "not confirmed" according to the following predefined algorithm:

Definite Event:

Confirmed by diagnostic measures with high specificity (e.g. phlebography for DVT, spiral CT for PE, cerebral MRT for cerebrovascular accidents, electrocardiogram (ECG) with typical ST-segment elevation for acute myocardial infarction, histology for gynecological cancer, two-sided blood pressure measurement with diastolic blood pressure of more than 120 mmHg for hypertensive crisis).

Probable Event:

Absence of confirmation by a diagnostic measure with high specificity, but clinical diagnosis confirmed by a health professional or supported by diagnostic tests with low specificity (such as D-dimer for VTE or typical ECG/blood gas tests for PE). These cases are usually characterized by a subsequent specific therapy (such as fibrinolysis or long-term anticoagulant therapy). However, if the attending physician confirms that the diagnosis is correct, the event was classified as a probable event even if specific treatment was not given.

Event not confirmed:

- The diagnosis reported by the patient is excluded by diagnostic procedures.
- A different medical condition is diagnosed by the attending physician.
- The participant did not contact a health care professional to clarify her symptoms and no diagnostic measures were performed that could have clarified the diagnosis.

The exposure data reported by the patients was validated via the prescribing physicians. Definite and probable events were classified as 'confirmed events'.

For VTE, the definition of "definite", "probable" and "not confirmed" is further specified:

Definite VTE: Confirmed by imaging procedure

- DVT: phlebography, duplex sonography, or magnetic resonance imaging (MRI).
- PE: pulmonary angiography, ventilation-perfusion scan, spiral computed tomography (CT), MRI, or transesophageal echocardiography.

Probable VTE:

Absence of confirmation by an imaging test, but a clinical diagnosis was confirmed by a health care professional or is supported by a non-imaging test (such as ultrasound doppler, plethysmography, D-dimer for VTE or typical ECG/blood gas tests for PE). These cases are usually characterized by a subsequent specific therapy (such as fibrinolysis or long-term anticoagulant therapy). However, if the attending physician confirmed that the diagnosis is correct, the event was classified as a probable VTE, even if a specific treatment was not given.

VTE not confirmed:

- VTE excluded by a physician.
- A different medical condition was diagnosed by the attending physician.
- Participant did not contact a health professional to clarify her symptoms and no diagnostic measures were performed that could have clarified the diagnosis.

For the final analysis this classification was verified by means of an independent blinded adjudication process.

Study Size

The sample size considerations were based on the expected VTE incidence for $COC_{LNG}$. Sample size calculations were based on an incidence rate of 10 VTE per 10,000 WY[1] for $COC_{LNG}$.

[1] 'idiopathic' PE and DVT of the lower extremities

The study was powered to test non-inferiority of NOMAC-E2 treatment regarding VTE risk in comparison to $COC_{LNG}$ use. The study was sufficiently powered to exclude a 1.5-fold VTE risk for NOMAC-E2 users compared to $COC_{LNG}$ users in the event that the true VTE risk among NOMAC-E2 users is not higher than among $COC_{LNG}$ users.

The sample size needed for the investigation of the VTE risk was also sufficient for the evaluation of secondary outcomes (with the exception of ATE). Acute myocardial infarction and stroke are very rare in a female population of reproductive age. The study was powered to exclude a 2.5-fold risk of ATE in NOMAC-E2 users compared to $COC_{LNG}$ users. This was sufficient to screen for safety signals and substantial effects.

Statistical Methods

Main Summary Measures

Incidence rates, crude HRs and adjusted HRs were calculated.

Main Statistical Methods

The study used a non-inferiority design to investigate the VTE risk of NOMAC-E2. The a priori assumption was that use of NOMAC-E2 is not associated with an increased risk of VTE compared to $COC_{LNG}$ (i.e. a statistical comparison of NOMAC-E2 and $COC_{LNG}$ is not expected to show a difference).

6. Results

Participants

A total of 101,498 women were enrolled in the study after having been recruited by 2,413 physicians in Australia, Austria, Colombia, France, Germany, Hungary, Italy, Mexico, Poland, Russia, Spain and Sweden. The results of the analyses presented herein are based on 102,330 women.

Descriptive Data

Of the 91,313 women in the AT population, a total of 44,559 were NOMAC-E2 users and 46,754 were $COC_{LNG}$ users (48.8% and 51.2% of the study population, respectively). Of the 46,754 $COC_{LNG}$ users, 20,181 (22.1% of the total study population) were users of a monophasic preparation containing 20 mcg of EE, 17,469 (19.1% of the total study population) were users of a monophasic preparation containing 30 mcg of EE and 9,104 (10% of the total study population) were users of multiphasic preparations.

At study entry, the mean age of NOMAC-E2 users was higher (31.0 years) than $COC_{LNG}$ users (29.3 years) and this difference was statistically significant ($p<0.0001$). There were no substantial differences in relation to mean weight (NOMAC-E2: 63.3 kg; $COC_{LNG}$: 63.1 kg) or mean BMI (NOMAC-E2: 23.2; $COC_{LNG}$: 23.3). The distribution of cohorts by age category is displayed in FIG. 1. Almost 33% of NOMAC-E2 users and 27% of $COC_{LNG}$ users were aged 35 or older.

As noted above, starters and restarters of COCs are included in the study population. Starters comprised 62.2% of NOMAC-E2 users and 64.4% of $COC_{LNG}$ users. Restarters comprised 37.8% and 35.6% of NOMAC-E2 and $COC_{LNG}$ users, respectively.

Characteristics associated with gynaecological history were largely similar between the cohorts at study entry. This included the mean age at menarche (12.8 years for each cohort), the mean age at first delivery among parous women (NOMAC-E2: 24.3 years; $COC_{LNG}$: 23.7 years), the median number of live births (if ever pregnant) (1.0 in each cohort) and the median number of miscarriages/stillbirths/abortions (if ever pregnant) (1.0 in each cohort). A greater proportion of NOMAC-E2 users reported ever having been pregnant (NOMAC-E2: 57.0%; $COC_{LNG}$: 54.9%).

In this real world observational study, women were asked for the reason(s) for their contraceptive prescription. With regard to the motivating factors behind COC use, 54.9% of NOMAC-E2 users reported seeking a COC prescription for contraceptive reasons only compared to 57.1% of $COC_{LNG}$ users. The proportions of women who reported contraceptive as well as non-contraceptive reasons were 33.9% and 33.1% for NOMAC-E2 and $COC_{LNG}$ users, respectively. Meanwhile, 9.5% of NOMAC-E2 users and 8.6% of $COC_{LNG}$ users reported using COCs exclusively for non-contraceptive reasons (such as cycle control, acne, painful and/or prolonged/heavy bleeding).

The non-contraceptive reasons specified by study participants are displayed in Table 1. Sometimes women reported more than one non-contraceptive reason.

TABLE 1

Non-contraceptive reasons for COC prescription reported by patients at study entry, by cohort

| | NOMAC-E2 (N = 50,187) | | $COC_{LNG}$ (N = 52,143) | | Total (N = 102,330) | |
|---|---|---|---|---|---|---|
| Patient-reported reason | n | % | n | % | n | % |
| Cycle regulation | 9,360 | 42.1 | 10,263 | 46.7 | 19,823 | 44.4 |
| Painful menstrual bleeding | 8,624 | 38.8 | 8,753 | 39.9 | 17,377 | 39.3 |
| Heavy and/or prolonged menstrual bleeding | 5,943 | 26.8 | 5,105 | 23.2 | 11,048 | 25.0 |
| Acne | 2,178 | 9.8 | 1,875 | 8.5 | 4,053 | 9.2 |
| Ovarian cysts | 1,784 | 8.0 | 1,838 | 8.4 | 3,622 | 8.2 |
| Polycystic ovary syndrome (PCOS) | 1,328 | 6.0 | 1,334 | 6.1 | 2,662 | 6.0 |
| Premenstrual syndrome (PMS) | 1,293 | 5.8 | 1,047 | 4.8 | 2,340 | 5.3 |
| Endometriosis | 1,335 | 6.0 | 863 | 3.9 | 2,198 | 5.0 |
| Bleeding on demand | 551 | 2.5 | 617 | 2.8 | 1,168 | 2.6 |
| Premenstrual dysphoric disorder (PMDD) | 217 | 1.0 | 143 | 0.7 | 360 | 0.8 |
| Other reasons | 1,572 | 7.1 | 1,338 | 6.1 | 2,910 | 6.6 |

Note:
Women could report multiple reasons.

At study entry, women were also asked about (i) history of treated depression; and (ii) history of acne. There were no significant differences between the cohorts. Women were also asked about their personal history of disease and regular medication use.

Outcome Data

Fatal Outcomes

A total of 30 study participants died during the study. Among the NOMAC-E2 users, 7 deaths were reported: 3 due to accidents, 2 due to cancer (one woman died of end stage lymphoma with metastasis to the liver and the other of vulvar cancer with widespread metastasis), 1 as a result of a systemic herpes infection and 1 due to an unknown cause.

Blinded to the hormonal contraceptive exposure status, the SMAC assessed that in 19 of the deaths there was no relationship to hormonal contraceptive use. One case involving a NOMAC-E2 user with a history of heart disease who died due to an unknown cause was assessed by the SMAC as having a possible relationship to hormonal contraceptive use because the cause of death was unknown. One case involving an Ex-user who died of an unknown cause was assessed as unlikely to be related to hormonal contraceptive use. In relation to another case involving an Ex-user who died of an unknown cause, the SMAC assessed the relationship with hormonal contraceptive use as 'indeterminate' because insufficient information is known to enable an assessment of a causal relationship.

SAEs

There were a total of 3,388 SAEs. An SAE is defined in this study as an adverse event that results in death, a life-threatening experience, inpatient hospitalization, persistent or significant disability/incapacity, or requires medical/surgical intervention to prevent one of these outcomes.

Figure 2:
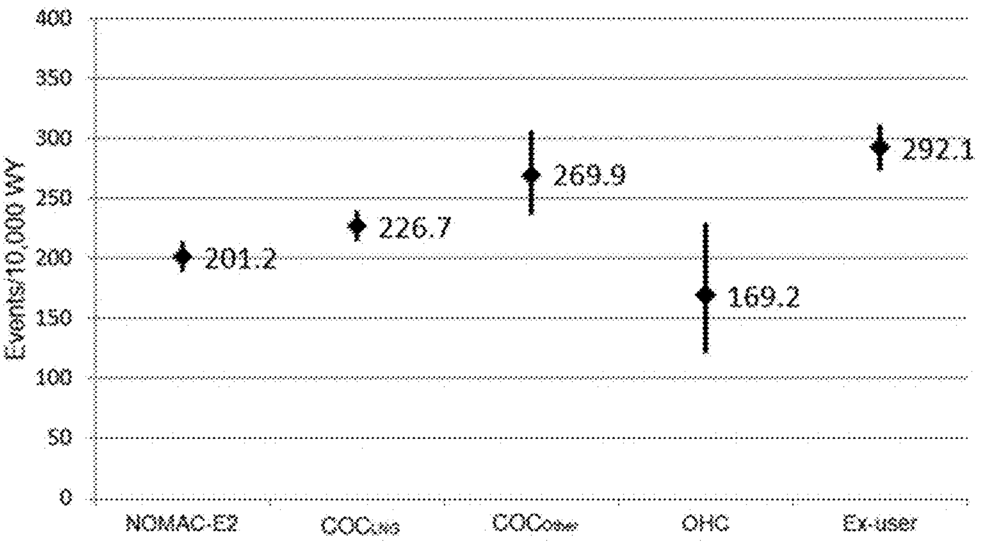
FIG. 2 shows the incidence of serious adverse effects (SAEs) observed in the study—according to COC or contraceptive used.

The incidence of SAE was lower in NOMAC-E2 users than in $COC_{LNG}$ users. Of 3,388 SAEs, 983 occurred in NOMAC-E2 users, 1,225 in $COC_{LNG}$ users, 224 in $COC_{Other}$ users, 40 in OHC users and 916 in ex-users. The corresponding incidence rates per 10,000 WY (and 95% confidence intervals) for each user cohort were as follows:

201.2 (189.0-214.1) for NOMAC-E2, 226.7 (214.3-239.6) for $COC_{LNG}$, 269.9 (236.1-307.0) for $COC_{Other}$, 169.2 (121.2-229.7) for OHC and 292.1 (273.8-311.4) for ex-users. FIG. 2 graphically displays the incidence rates and 95% confidence intervals.

Malignant Neoplasm

A comparison of the user (sub-) cohorts showed no relevant difference: 41 NOMAC-E2 (8.4 per 10,000 WY; 95% CI, 6.0-11.4), 43 $COC_{LNG}$ (8.0 per 10,000 WY; 95% CI, 5.8-10.7), 5 $COC_{Other}$ (6.0 per 10,000 WY; 95% CI, 2.0-14.1), 1 OHC (4.2 per 10,000 WY; 95% CI, 0.1-23.5) and 40 ex-users (12.8 per 10,000 WY; 95% CI, 9.1-17.4). The most frequent cases involved breast cancer: 11 NOMAC-E2 (2.3 per 10,000 WY; 95% CI, 1.1-4.0), 13 $COC_{LNG}$ (2.4 per 10,000 WY; 95% CI, 1.3-4.1), 4 $COC_{Other}$ (4.8 per 10,000 WY; 95% CI, 1.3-12.3), 1 OHC (4.2 per 10,000 WY; 95% CI, 0.1-23.5) and 19 ex-users (6.1 per 10,000 WY; 95% CI, 3.6-9.5).

Main Results

During the reporting period, data from a total of 144,901 WY WY of observation were collected. In addition to the cohorts at study entry (NOMAC-E2 and $COC_{LNG}$), a number of additional cohorts developed during the follow-up phase as women switched to other forms of contraception or discontinued contraceptive use altogether. Table 2 displays the number of WY within each of the user cohorts.

TABLE 2

Number of WY of observation within each (sub)-cohort

| User (sub-)cohort | Woman years | Percentage of observation time |
|---|---|---|
| NOMAC-E2 | 48,846 | 33.7 |
| $COC_{LNG}$ | 54,037 | 37.3 |
| $COC_{Other}$ | 8,300 | 5.7 |
| Other hormonal contraceptive (OHC)* | 2,364 | 1.6 |
| Ex-user (no hormonal contraceptive use) | 31,354 | 21.6 |
| Total | 144,901 | 100** |

*Progestin-only OC, vaginal ring, injection, intrauterine device, contraceptive patch or implant.
**Discrepancy due to rounding.

Primary Outcome of Interest

DVT of the Lower Extremities and PE

Figure 3:
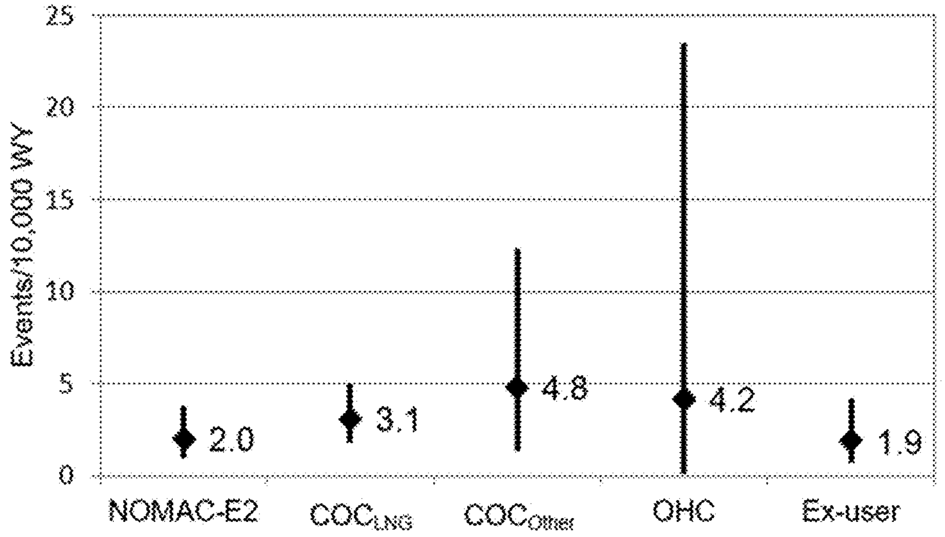
FIG. 3 shows the incidence of deep vein thrombosis (DVT) of the lower extremities and pulmonary embolism (PE). The incidence rates per 10,000 WY and 95% confidence intervals per (sub)-cohort are shown.

Overall, there have been 38 confirmed VTE comprising the primary outcome of interest (DVT of the lower extremities and PE): 10 in NOMAC-E2 users (2.0 per 10,000 WY; 95% CI, 1.0-3.8), 17 in $COC_{LNG}$ users (3.1 per 10,000 WY; 95% CI, 1.8-5.0), 4 in $COC_{Other}$ users (4.8 per 10,000 WY; 95% CI, 1.3-12.3), 1 in an OHC user (4.2 per 10,000 WY; 95% CI, 0.1-23.5) and 6 in ex-users (1.9 per 10,000 WY; 95% CI, 0.7-4.2) (FIG. 3). Five women (2 $COC_{LNG}$ users and 3 $COC_{Other}$ users) experienced both a DVT of a lower extremity and a PE. The point estimates and 95% confidence intervals per user (sub)-cohort are in Table 3.

TABLE 3

DVT of the lower extremities and PE: Numbers, incidence rates per 10,000 WY and 95% confidence intervals per (sub-)cohort

| | NOMAC-E2 (48,846 WY) | | $COC_{LNG}$ (54,037 WY) | | $COC_{other}$ (8,300 WY) | | OHC (2,364 WY) | | Ex-user (31,364 WY) | | Total (144,901 WY) | |
|---|---|---|---|---|---|---|---|---|---|---|---|---|
| Category | n | Incidence** (95% CI) | n | Incidence** (95% CI) | n | Incidence** (95% CI) | n | Incidence** (95% CI) | n | Incidence** (95% CI) | n | Incidence** (95% CI) |
| DVT of lower extremities and PE | 10 | 2.0 (1.0-3.8) | 17 | 3.1 (1.8-5.0) | 4 | 4.8 (1.3-12.3) | 1 | 4.2 (0.1-23.5) | 6 | 1.9 (0.7-4.2) | 38 | 2.8 (1.9-3.8) |
| Thereof: | | | | | | | | | | | | |
| DVT | 7 | 1.4 (0.6-3.0) | 12 | 2.2 (1.1-3.9) | 4 | 4.8 (1.3-12.3) | 0 | 0.0 (0.0-15.6) | 2 | 0.6 (0.1-2.3) | 25 | 1.7 (1.1-2.5) |
| PE | 3 | 0.6 (0.1-1.8) | 7 | 1.3 (0.5-2.7) | 3 | 3.6 (0.75-10.8) | 1 | 4.2 (0.1-23.5) | 4 | 1.3 (0.35-3.3) | 18 | 1.2 (0.7-2.0) |

*Pregnant within 3 months of treatment initiation, history of cancer/chemotherapy or an increased genetic risk of VTE (e.g. Factor V Leiden. Protein S or C deficiency).
**Incidence rate per 10,000 WY
Note:
Five women (2 $COC_{LNG}$ users and 3 $COC_{other}$ users) experienced both a DVT and a PE.

Figure 4:
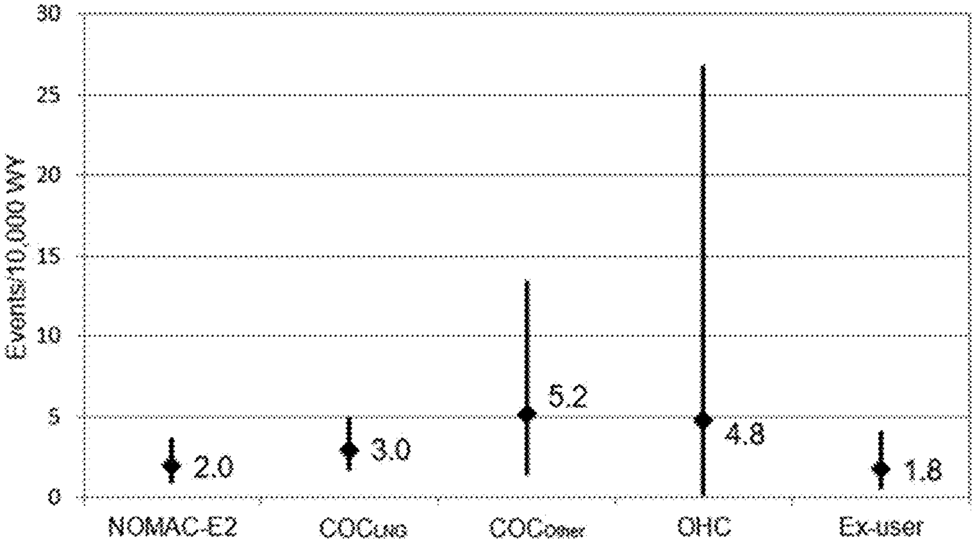
FIG. 4 shows deep vein thrombosis (DVT) of the lower extremities and pulmonary embolism (PE) among women without known pre-defined risk factors at baseline. The incidence rates per 10,000 WY and 95% confidence intervals per (sub)-cohort are shown.

DVT of the Lower Extremities and PE after Excluding Women with Pre-Defined Risk Factors at Study Entry Risk estimates of VTE may be influenced by women who are pregnant within 3 months of treatment initiation, have a history of cancer/chemotherapy or an increased genetic risk of VTE (e.g. Factor V Leiden, Protein S or C deficiency). Therefore, an analysis was planned which would exclude all women who reported these pre-defined risk factors at study entry. This resulted in the exclusion of 4 VTE being excluded from the analysis: 2 $COC_{LNG}$ users and 1 ex-user who had been pregnant within 3 months of study entry and 1 NOMAC-E2 user who had a history of cancer/chemotherapy. Therefore, this analysis was based on 34 confirmed VTE comprising the primary outcome of interest (DVT of the lower extremities and PE): 9 in NOMAC-E2 users (2.0 per 10,000 WY; 95% CI, 0.9-3.7), 15 in $COC_{LNG}$ users (3.0 per 10,000 WY; 95% CI, 1.7-5.0), 4 in $COC_{Other}$ users (5.2 per 10,000 WY; 95% CI, 1.4-13.4), 1 in an OHC user (4.8 per 10,000 WY; 95% CI, 0.1-26.8) and 5 in ex-users (1.8 per 10,000 WY; 95% CI, 0.6-4.1) (FIG. 4). The number of (primary outcome) VTE, point estimates and 95% confidence intervals for the (sub)-cohorts are presented in Table 4.

TABLE 4

DVT of the lower extremities and PE among women without known pre-defined risk factors at baseline: Numbers, incidence rates per 10,000 WY and 95% confidence intervals per (sub)-cohort

| | NOMAC-E2 (45,750 WY) | | $COC_{LNG}$ (49,729 WY) | | $COC_{Other}$ (7,620 WY) | | OHC (2,073 WY) | | Ex-user (28,372 WY) | | Total (133,544 WY) | |
|---|---|---|---|---|---|---|---|---|---|---|---|---|
| Category | n | Incidence** (95% CI) | n | Incidence** (95% CI) | n | Incidence** (95% CI) | n | Incidence** (95% CI) | n | Incidence** (95% CI) | n | Incidence** (95% CI) |
| DVT of lower extremities and PE Thereof: | 9 | 2.8 (0.9-3.7) | 15 | 3.0 (1.7-5.0) | 4 | 5.2 (1.4-13.4) | 1 | 4.8 (0.1-26.8) | 5 | 1.8 (0.6-4.1) | 34 | 2.5 (1.8-3.6) |
| DVT | 6 | 1.3 (0.5-2.9) | 11 | 2.2 (1.1-4.0) | 4 | 5.2 (1.4-13.4) | 0 | 0.0 (0.0-17.8) | 1 | 0.35 (0.01-2.0) | 22 | 1.6 (1.0-2.5) |
| PE | 3 | 0.7 (0.1-1.9) | 6 | 3.2 (0.4-2.6) | 3 | 3.8 (0.8-11.5) | 1 | 4.8 (0.1-26.8) | 4 | 1.4 (0.4-3.6) | 17 | 1.3 (0.7-2.0) |

* Women who were pregnant within 3 months of treatment initiation, had a history of cancer/chemotherapy or an increased genetic risk of VTE (e.g. Factor V Leiden, Protein S or C deficiency).
**Incidence rate per 10,000 WY
Note:
Five women (2 $COC_{LNG}$ users and 3 $COC_{Other}$ users) experienced both a DVT and a PE.

NOMAC-E2 use does not appear to be associated with a higher risk of VTE compared with the use of other COCs. The $HR_{crude}$ for NOMAC-E2 vs. $COC_{LNG}$ of 0.65 with a 95% confidence interval of 0.28-1.48. After adjusting for age, BMI, family history of VTE and current duration of HC use, $HR_{adj}$ was 0.59 (95% CI, 0.25-1.35).

TABLE 5

DVT of the lower extremities and PE among women who reported at study entry that their motivation for NOMAC-E2 or $COC_{LNG}$ use was for contraceptive reasons only: Numbers, incidence rates per 10,000 WY and 95% confidence intervals per (sub)-cohort

| | NOMAC-E2 (24,354 WY) | | $COC_{LNG}$ (27,433 WY) | | $COC_{Other}$ (3,554 WY) | | OHC (1,043 WY) | | Ex-user (13,020 WY) | | Total (69,414 WY) | |
|---|---|---|---|---|---|---|---|---|---|---|---|---|
| Category | n | Incidence*** (95% CI) | n | Incidence*** (95% CI) | n | Incidence*** (95% CI) | n | Incidence*** (95% CI) | n | Incidence*** (95% CI) | n | Incidence*** (95% CI) |
| DVT of lower extremities and PE Thereof: | 4 | 1.6 (0.45-4.2) | 10 | 3.6 (1.7-6.7) | 1 | 2.8 (0 1-15.7) | 0 | 0.0 (0 0-35.3) | 2 | 1.5 (0.2-5.5) | 17 | 2.4 (1.4-3.9) |
| DVT | 2 | 0.8 (0.1-3.0) | 6 | 2.2 (0.8-4.8) | 1 | 2.8 (0.1-15.7) | 0 | 0.0 (0.0-35.3) | 1 | 0.8 (0.0-4.3) | 10 | 1.4 (0.7-2.6) |
| PE | 2 | 0.8 (0.1-3.0) | 6 | 2.2 (0.8-4.8) | 1 | 2.8 (0 1-15.7) | 0 | 0.0 (0 0-35.3) | 1 | 0.8 (0.0-4.3) | 10 | 1.4 (0.7-2.8) |

*Pregnant within 3 months of treatment intiation, history of cancer/chemotherapy or an increased genetic risk of VTE (e.g. Factor V Leiden, Protein S or C deficiency).
**Reasons(s) for contraceptive use were captured only at study entry and were not necessarily relevant at the time of the event.
***Incidence rate per 10,000 WY
Note:
Three women (2 $COC_{LNG}$ users and 1 $COC_{Other}$ user) experienced botha DVT and a PE.

Multiple imputation analysis resulted in an $HR_{crude}$ for NOMAC-E2 vs. $COC_{LNG}$ of 0.65 (95% CI, 0.28-1.48). After adjusting for age, BMI (multiple imputation), family history of VTE and current duration of HC use, the $HR_{adj}$ was 0.59 (95% CI, 0.25-1.35).

DVT of the Lower Extremities and PE Limited to Women Using COCs for Contraceptive Purposes Only An analysis was performed which was limited to women who reported that their motivation for their prescription at study entry was for contraceptive reasons only.

Figure 5:
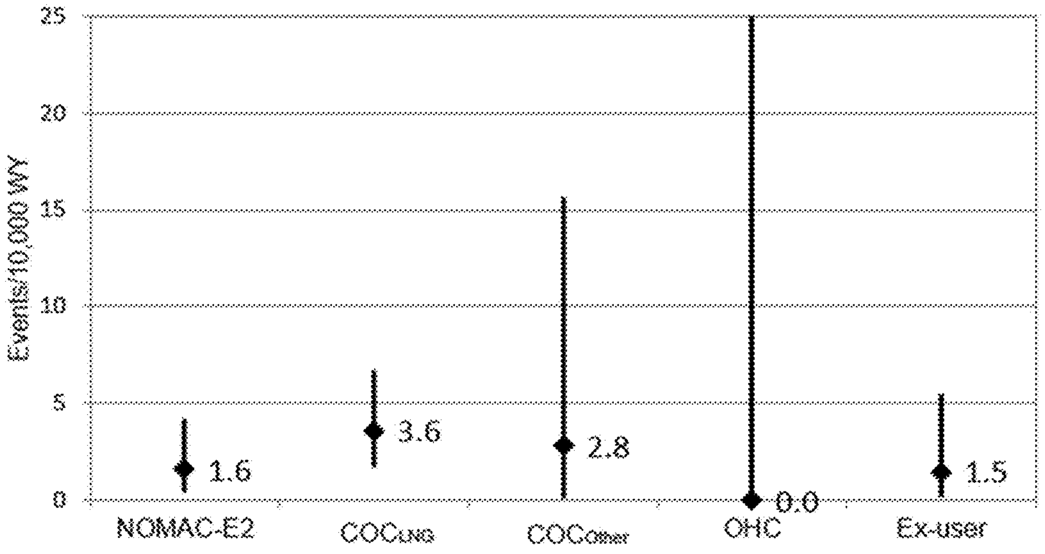
FIG. 5 shows deep vein thrombosis (DVT) of the lower extremities and pulmonary embolism (PE) among women using a COC for contraceptive reasons only. The incidence rates per 10,000 WY and 95% confidence intervals per (sub)-cohort are shown.

There were a total of 17 VTEs (2.4 per 10,000 WY; 95% CI, 1.4-3.9) in women who reported that their motivation for using the COC was for contraceptive reasons only: 4 VTEs in NOMAC-E2 users (1.6 per 10,000 WY; 95% CI, 0.45-4.2), 10 VTEs in $COC_{LNG}$ users (3.6 per 10,000 WY; 95% CI, 1.7-6.7), 1 VTE in a $COC_{Other}$ user (2.8 per 10,000 WY; 95% CI, 0.1-15.7) and 2 VTEs in ex-users (1.5 per 10,000 WY; 95% CI, 0.2-5.5) (FIG. 5). Table 5 displays the number of VTE, point estimates and 95% confidence intervals for the (sub)-cohorts.

DVT of the Lower Extremities and PE by Geographical Region Excluding Russia

The low overall incidence rate of DVT of the lower extremities and PE observed in this study (2.5 per 10,000 WY; 95% CI, 1.8-3.6) can mainly be explained by the particularly low rate of VTE observed in the Russian study participants who comprise a large proportion (39.5%) of the PRO-E2 study population.

Figure 6:
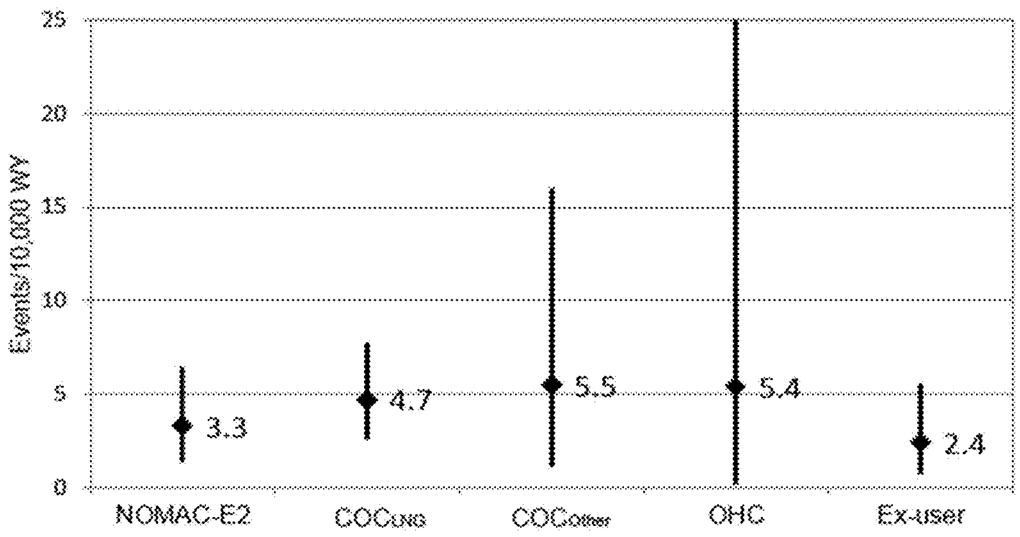
FIG. 6 shows deep vein thrombosis (DVT) of the lower extremities and pulmonary embolism (PE) excluding women recruited to the study from Russia. The incidence rates per 10,000 WY and 95% confidence intervals per (sub)-cohort are shown.

If Russia is excluded from the VTE analysis, the resulting incidence rates are 3.3 per 10,000 WY (95% CI, 1.4-6.5) for NOMAC-E2 and 4.7 per 10,000 WY (95% CI, 2.6-7.8) for $COC_{LNG}$ (FIG. 6).

Excluding Australia, Colombia and Mexico

Analysis of the primary endpoint in which data from Australia, Colombia and Mexico were excluded, resulted in the calculation of risk estimates based on 33 VTE: 9 in NOMAC-E2 users (2.0 per 10,000 WY; 95% CI, 0.9-3.9), 14 in $COC_{LNG}$ users (3.0 per 10,000 WY; 95 CI, 1.7-5.1), 4 in $COC_{Other}$ users (5.4 per 10,000 WY; 95% CI, 1.5-13.7) and 5 in Ex-users (1.8 per 10,000 WY; 95% CI, 0.6-4.3).

DVT of the Lower Extremities and PE by User Status (Starters Vs Restarters)

A stratified analysis of VTE per user status (starters, restarters) did not indicate a higher VTE risk for NOMAC-E2. There were 16 VTEs (DVT of the lower extremities and PE) among starters: 5 in NOMAC-E2 users (1.7 per 10,000 WY; 95% CI, 0.6-4.0), 6 in $COC_{LNG}$ users (1.9 per 10,000 WY; 95% CI, 0.7-4.1), 3 in $COC_{Other}$ users (7.4 per 10,000 WY; 95% CI, 1.5-21.7) and 2 in ex-users (1.3 per 10,000 WY; 95% CI, 0.15-4.6). There were 18 VTEs (DVT of the lower extremities and PE) among restarters: 4 in NOMAC-E2 users (2.4 per 10,000 WY; 95% Cl, 0.6-6.1), 9 in $COC_{LNG}$ users (5.0 per 10,000 WY; 95% CI, 2.3-9.5), 1 in a $COC_{Other}$ user (2.8 per 10,000 WY; 95% CI, 0.1-15.5), 1 in an OHC user (9.4 per 10,000 WY; 95% CI, 0.2-52.4) and 3 in ex-users (2.4 per 10,000 WY; 95% CI, 0.5-6.9).

DVT of the Lower Extremities and PE by Type of Preparation (Monophasic Vs Multiphasic)

The risk of VTE in NOMAC-E2 users was compared with the risk in users of monophasic $COC_{LNG}$ preparations containing 20 mcg EE ($COC_{LNGMono/20\ mcg}$), $COC_{LNG}$ preparations containing 30 mcg EE ($COC_{LNGMono/30\ mcg}$) and in users of multiphasic $COC_{LNG}$ preparations ($COC_{LNGMulti}$). There were 9 VTEs in NOMAC-E2 users (2.0 per 10,000 WY; 95% CI 0.9-3.7), 11 in $COC_{LNGMono/20\ mcg}$ users (4.9 per 10,000 WY; 95% CI, 2.4-8.7), 1 in a $COC_{LNGMono/30\ mcg}$ user (0.6 per 10,000 WY; 95% Cl, 0.0-3.2) and 3 in $COC_{LNGMulti}$ users (3.2 per 10,000 WY; 95% CI, 0.7-9.3).

Hazard ratios (crude and after adjusting for age, BMI, family history of VTE and current duration of use) were calculated. A comparison of NOMAC-E2 to monophasic $COC_{LNG}$ preparations with 20 mcg EE resulted in an $HR_{crude}$ of 0.4 (95% CI, 0.1-1.1) and the $HR_{adj}$ was 0.3 (95% CI, 0.1-1.0). The $HR_{crude}$ for NOMAC-E2 vs. $COC_{LNGMono/30\ mcg}$ was 2.5 (95% CI, 0.3-20.6) and the $HR_{adj}$ was 2.6 (95% CI, 0.3-21.4). The $HR_{crude}$ for NOMAC-E2 vs. $COC_{LNGMulti}$ was 0.5 (95% Cl, 0.1-1.8) and the $HR_{adj}$ was 0.4 (95% CI, 0.1-1.6).

Secondary Outcomes of Interest

All VTE

Figure 7:
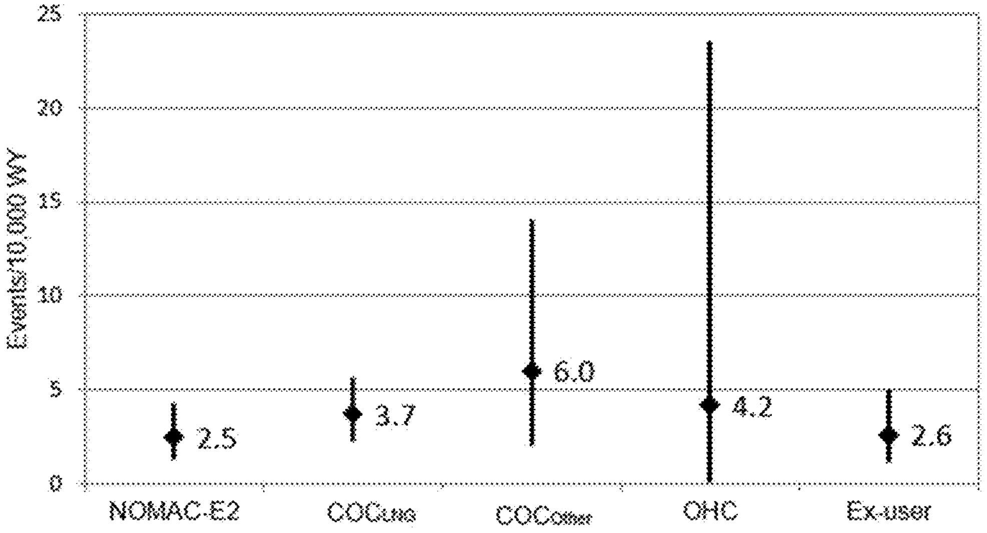
FIG. 7 shows all instances of venous thromboembolism (VTE), in which the incidence rates per 10,000 WY and 95% confidence intervals per (sub)-cohort are shown.

A total of 46 VTEs were confirmed. In addition to the 38 VTEs comprising a DVT of the lower extremities or PE (the primary outcome of interest) referred to in Table 33, there were 8 additional DVTs: 2 in NOMAC-E2 users (1 in the arm and 1 in the portal vein), 3 in $COC_{LNG}$ users (2 in the arm and 1 in the sinus vein), 1 in a $COC_{Other}$ user (in the arm) and 2 in ex-users (both in the subclavian vein). The numbers and incidence rates for each (sub-) cohort were as follows: NOMAC-E2 12 VTEs (2.5 per 10,000 WY; 95% CI, 1.3-4.3), $COC_{LNG}$ 20 VTEs (3.7 per 10,000 WY; 95% CI, 2.3-5.7), $COC_{Other}$ 5 VTEs (6.0 per 10,000 WY; 95% CI, 2.0-14.1), OHC 1 VTE (4.2 per 10,000 WY; 95% CI, 0.1-23.5) and ex-users 8 VTEs (2.6 per 10,000 WY; 95% Cl, 1.1-5.0) (FIG. 7).

Idiopathic VTE

Overall, 35 of the 46 confirmed VTEs were considered idiopathic VTEs. The numbers and incidence rates for each (sub-) cohort are as follows: NOMAC-E2 10 VTEs (2.0 per 10,000 WY; 95% CI, 1.0-3.8), $COC_{LNG}$ 15 VTEs (2.8 per 10,000 WY; 95% CI, 1.6-4.6), $COC_{Other}$ 5 VTEs (6.0 per 10,000 WY; 95% CI, 2.0-14.1), OHC 1 VTE (4.2 per 10,000 WY. 95% CI, 0.1-23.5) and ex-users 4 VTEs (1.3 per 10,000 WY; 95% CI, 0.35-3.3).

Summary of VTE Results

A summary of the results of the numerous analyses which were conducted to evaluate the risk of VTE in NOMAC-E2 users compared with $COC_{LNG}$ users is displayed in Table 7.

TABLE 6 displays the number of VTE, point estimates and 95% confidence intervals for the (sub)-cohorts.

| | NOMAC-E2 (48,846 WY) | | $COC_{LNG}$ (54.037 WY) | | $COC_{Other}$ (8,300 WY) | | OHC (2,364 WY) | | Ex-user (31,354 WY) | | Total (144,901 WY) | |
|---|---|---|---|---|---|---|---|---|---|---|---|---|
| Category | n | Incidence* (95% CI) | n | Incidence* (95% CI) | n | Incidence* (95% CI) | n | Incidence* (95% CI) | n | Incidence* (95% CI) | n | Incidence* (95% CI) |
| ALL VTE | 12 | 2.5 (1.3-4.3) | 20 | 3.7 (2.3-5.7) | 5 | 6.0 (2.0-14.1) | 1 | 4.2 (0.1-23.5) | 8 | 2.8 (1.1-5.0) | 46 | 3.2 (2.3-4.2) |
| Thereof: | | | | | | | | | | | | |
| DVT of lower extremities and PE | 10 | 2.0 (1.0-3.8) | 17 | 3.1 (1.8-5.0) | 4 | 4.8 (1.3-12.3) | 1 | 4.2 (0.1-23.5) | 6 | 1.9 (0.7-4.2) | 38 | 2.8 (1.9-3.6) |
| All other DVT | 2 | 0.4 (0.05-1.5) | 3 | 0.56 (0.1-1.6) | 1 | 1.2 (0.0-6.7) | 0 | 0.0 (0.0-15.6) | 2 | 0.6 (0.1-2.3) | 8 | 0.55 (0.2-1.1) |

*Incidence rate per 10,000 WY

TABLE 7

Summary of results of VTE analyses: Numbers, events, incidence rates per 10,000 WY and 95% confidence intervals in NOMAC-E2 users and $COC_{LNG}$ users

| | NOMAC-E2 | | $COC_{LNG}$ | |
|---|---|---|---|---|
| Category | n | Incidence* (95% CI) | n | Incidence* (95% CI) |
| Primary outcome (DVT lower extremities and PE) | | | | |
| Main analysis (excluding women with pre-defined risk factors** at study entry) | 9 | 2.0 (0.9-3.7) | 15 | 3.0 (1.7-5.0) |

TABLE 7-continued

Summary of results of VTE analyses: Numbers, events, incidence rates per 10,000 WY and 95% confidence intervals in NOMAC-E2 users and $COC_{LNG}$ users

| | NOMAC-E2 | | $COC_{LNG}$ | |
|---|---|---|---|---|
| Category | n | Incidence* (95% CI) | n | Incidence* (95% CI) |
| Adolescents only | 0 | 0.0 (0.0-21.3) | 2 | 5.9 (0.7-21.4) |
| Excluding Russia | 8 | 3.3 (1.4-6.5) | 15 | 4.7 (2.6-7.8) |
| Excluding Australia and Latin America | 9 | 2.0 (0.9-3.9) | 14 | 3.0 (1.7-5.1) |
| Including Mexico | 9 | 1.9 (0.9-3.7) | 15 | 3.0 (1.7-5.0) |
| Starters only | 5 | 1.7 (0.56-4.0) | 6 | 1.9 (0.7-4.1) |
| Restarters only | 4 | 2.4 (0.6-6.1) | 9 | 5.0 (2.3-9.5) |
| Including ICD-10 code I80.3*** | 10 | 2.2 (1.0-4.0) | 16 | 3.2 (1.8-5.2) |
| Allocation of one VTE to $COC_{Other}$ rather than NOMAC-E2 | 8 | 1.7 (0.75-3.4) | 15 | 3.0 (1.7-5.0) |
| COC used for contraceptive reasons only | 4 | 1.6 (0.45-4.2) | 10 | 3.6 (1.7-6.7) |
| Monophasic $COC_{LNG}$ with 20 mcg EE | 9 | 2.0 (0.9-3.7) | 11 | 4.9 (2.4-8.7) |
| Monophasic $COC_{LNG}$ with 30 mcg EE | 9 | 2.0 (0.9-3.7) | 1 | 0.6 (0.01-3.2) |
| Multiphasic $COC_{LNG}$ | 9 | 2.0 (0.9-3.7) | 3 | 3.2 (0.66-9.3) |
| Including women with pre-defined risk factors** at study entry) | 10 | 2.0 (0.98-3.8) | 17 | 3.1 (1.8-5.0) |
| Secondary outcome (All VTE) | 12 | 2.5 (1.3-4.3) | 20 | 3.7 (2.3-5.7) |
| Confirmed and possible VTE | 14 | 2.9 (1.6-4.8) | 21 | 3.9 (2.4-5.9) |
| Confirmed, possible and potential VTE | 20 | 4.1 (2.5-5.3) | 28 | 5.2 (3.4-7.5) |
| Secondary outcome (Idiopathic VTE) | 10 | 2.0 (0.98-3.8) | 15 | 2.8 (1.6-4.6) |

*Incidence rate per 10,000 WY

**Pregnant within 3 months of treatment initiation, history of cancer/chemotherapy or an increased genetic risk for VTE (e.g. Factor V Leiden, Protein S or C deficiency) at baseline.

***Phlebitis and thrombophlebitis lower extremities, unspecified.

Other Secondary Outcomes

There were 289 unintended pregnancies in hormonal contraceptive users: 64 NOMAC-E2 (0.15 per 100 WY; 95% CI, 0.11-0.19), 200 $COC_{LNG}$ (0.41 per 100 WY; 95% CI, 0.35-0.47), 19 $COC_{Other}$ (0.26 per 100 WY; 95% CI, 0.16-0.40) and 6 OHC (0.28 per 100 WY; 95% CI, 0.10-0.61). Unintended pregnancy was statistically significantly less likely in NOMAC-E2 users compared to $COC_{LNG}$ users ($p<0.0001$).

A total of 16 ATEs were confirmed: 4 ATEs (2 ischemic strokes, 1 TIA and 1 myocardial infarction) in NOMAC-E2 users (0.8 per 10,000 WY; 95% CI, 0.2-2.1), 7 ATEs (4 ischemic strokes and 3 AMI) in $COC_{LNG}$ users (1.3 per 10,000 WY; 95% CI, 0.5-2.7), 1 ATE (an AMI) in a $COC_{Other}$ user (1.2 per 10,000 WY; 95% CI, 0.0-6.7) and 4 ATEs (3 ischemic strokes and 1 AMI) in ex-users (1.3 per 10,000 WY; 95% CI, 0.35-3.3).

There were 24 cases of inflammatory bowel disease. The numbers and incidences per (sub-) cohort were as follows: 4 in NOMAC-E2 users (0.8 per 10,000 WY; 95% CI, 0.2-2.1), 13 in $COC_{LNG}$ users (2.4 per 10,000 WY; 95% CI, 1.3-4.1), 3 in $COC_{Other}$ users (3.6 per 10,000 WY; 95% CI, 0.75-10.6) and 4 in ex-users (1.3 per 10,000 WY; 95% CI, 0.35-3.3).

There were 261 cases of cholelithiasis (18.0 per 10,000 WY; 95% CI, 15.9-20.3): 84 NOMAC-E2 (17.2 per 10,000 WY; 95% CI, 13.7-21.3), 92 $COC_{LNG}$ (17.0 per 10,000 WY; 95% CI, 13.7-20.9), 21 $COC_{Other}$ (25.3 per 10,000 WY; 95% CI, 15.7-38.6), 8 OHC (33.8 per 10,000 WY; 95% CI, 14.6-66.6) and 56 ex-users (17.9 per 10,000 WY; 95% CI, 13.5-23.2) There were 24 cases of inflammatory bowel disease: 4 NOMAC-E2 (0.8 per 10,000 WY; 95% CI, 0.2-2.1), 13 $COC_{LNG}$ (2.4 per 10,000 WY; 95% CI, 1.3-4.1), 3 $COC_{Other}$ (3.6 per 10,000 WY; 95% CI, 0.75-10.6) and 4 ex-users (1.3 per 10,000 WY; 95% CI, 0.35-3.3).

Of the 191 cases of general hepatobiliary disorders, 65 were in NOMAC-E2 users (13.3 per 10,000 WY; 95% CI, 10.3-17.0), 63 in $COC_{LNG}$ users (11.7 per 10,000 WY; 95% CI, 9.0-14.9), 12 in $COC_{Other}$ users (14.5 per 10,000 WY; 95% CI, 7.5-25.2), 6 in OHC users (25.4 per 10,000 WY; 95% CI, 9.3-55.2) and 45 in ex-users (14.4 per 10,000 WY; 95% CI, 10.5-19.2).

There were 188 cases of new depression or worsening of an existing depression: 46 cases in NOMAC-E2 users (9.4 per 10,000 WY; 95% CI, 6.9-12.6), 80 in $COC_{LNG}$ users (14.8 per 10,000 WY; 95% CI, 11.7-18.4), 13 in $COC_{Other}$ users (15.7 per 10,000 WY; 95% CI, 8.3-26.8), 8 in OHC users (33.8 per 10,000 WY; 95% CI, 14.6-66.6) and 41 in ex-users (13.1 per 10,000 WY; 95% CI, 9.4-17.7).

Mean body weight increased modestly between each follow-up time point (6, 12 and 24 months after study entry) in comparison with baseline for both NOMAC-E2 and $COC_{LNG}$ users. In general, NOMAC-E2 users appeared to experience more of an improvement in their acne during follow-up (in comparison with baseline) than $COC_{LNG}$ users.

Review of Power Calculations

The sample size calculations specified in the study protocol were based on an incidence of 10 VTE per 10,000 WY for $COC_{LNG}$. Sample size calculations for a non-inferiority test of two exponential survival curves showed that an expected number of 150 VTE cases would be sufficient to reach this goal. These calculations were based on the following assumptions: 1) one-sided a of 0.05; 2) power (1-β) of 0.80 and 3) non-inferiority limit on a HR of 1.5. At an incidence rate of 10/10,000 WY a total of 150 VTE could be expected within 150,000 WY.

The results presented herein indicate that at this point in time, the risk of VTE is not equal among NOMAC-E2 users and $COC_{LNG}$ users. In relation to the primary outcome of interest (DVT of the lower extremities and PE) among women without pre-defined risk factors at study entry, the $HR_{crude}$ for NOMAC-E2 vs. $COC_{LNG}$ is 0.6 with a 95% confidence interval of 0.2 to 1.5. After adjusting for age, BMI, family history of VTE and current duration of use, the $HR_{adj}$ for NOMAC-E2 vs. $COC_{LNG}$ remained 0.6 (0.2-1.5).

Interpretation

These results demonstrate that NOMAC-E2 users are not at higher risk of ATE, death, SAE, cholelithiasis, inflammatory bowel disease, general hepatobiliary disorders, depressive disorders, mood changes, weight changes or acne changes compared to $COC_{LNG}$ users. They also demonstrate the NOMAC-E2 users are at a reduced risk of unintended pregnancy compared to $COC_{LNG}$ users.

Generalisation

The study was designed to reflect routine clinical use of COCs. Study participants were recruited by COC-prescribing healthcare professionals (e.g. gynecologists, general practitioners, midwives) and all new users of COCs could participate in the study. Participation was not limited by medical inclusion and exclusion criteria. Therefore, the ability to generalize the results of this study is high.

7. Summary

Baseline Characteristics

NOMAC-E2 users had a higher mean age at study entry compared to $COC_{LNG}$ users. Other baseline characteristics (including cardiovascular risk factors) were similar between the user cohorts. The similarities between the cohorts would indicate that confounding should be minimal.

Primary Outcome of Interest

The risk of DVT of the lower extremities and PE (VTE) was lower in the NOMAC-E2 cohort (2.0 per 10,000 WY; 95% CI, 0.9-3.7), compared to the $COC_{LNG}$ cohort (3.0 per 10,000 WY; 95% CI, 1.7-5.0).

The $HR_{crude}$ for NOMAC-E2 vs. $COC_{LNG}$ was 0.65 with a 95% confidence interval of 0.28 to 1.48. After adjusting for age, BMI, family history of VTE and current duration of use, $HR_{adj}$ remained 0.6 (95% CI, 0.25-1.35).

$COC_{LNG}$ are considered to be one of the CHCs associated with the lowest risk of VTE in patients and consequently are used as first line CHCs. This study reports for the first time that NOMAC-E2 is associated with a lower risk of VTE compared to $COC_{LNG}$. Therefore, this study supports the use of NOMAC-E2 as a first line CHC.

Secondary Outcomes of Interest

The risk of all VTE was lower in the NOMAC-E2 cohort (2.5 per 10,000 WY; 95% CI, 1.3-4.3) compared to the $COC_{LNG}$ cohort (3.7 per 10,000 WY; 95% CI, 2.3-5.7).

The risk of idiopathic VTE was lower in NOMAC-E2 users (2.0 per 10,000 WY; 95% CI, 1.0 3.8) compared to $COC_{LNG}$ users (2.8 per 10,000 WY; 95% CI, 1.6-4.6).

There were no statistically significant differences between NOMAC-E2 users and $COC_{LNG}$ users in relation to the risk of ATE, cholelithiasis, inflammatory bowel disease, general hepatobiliary disorders, depressive disorders, mood changes, weight or acne.

The risk of unintended pregnancy was statistically significantly lower in the NOMAC-E2 cohort (0.15 per 100 WY; 95% CI, 0.11-0.19) than the $COC_{LNG}$ cohort (0.41 per 100 WY; 95% CI, 0.35-0.47) ($p<0.0001$).

The invention claimed is:

1. A method of contraception, comprising:

(i) identifying a woman desirous of contraception as suitable for receiving a combined hormonal contraceptive (CHC);

(ii) selecting a CHC, wherein the selected CHC has been identified as a CHC associated with lowest risk of venous thromboembolism (VTE), wherein the selected CHC is a combined oral contraceptive (COC) composition comprising nomegestrol acetate and estradiol or an ester thereof; and (iii) providing the COC composition comprising nomegestrol acetate and estradiol or an ester thereof to the woman desirous of contraception;

wherein the woman desirous of contraception is selected from at least one of the following: a woman who has been pregnant within the past 3 months, a woman who has or has had cancer, a woman who is having or has had chemotherapy treatment, and a woman who has an increased genetic risk of VTE, and wherein the woman desirous of contraception achieves a risk of VTE that is reduced by at least about 10% compared to a reference risk of VTE for a COC containing levonorgestrel.

2. The method according to claim 1, further comprising step (i-a) between steps (i) and (ii), wherein step (i-a) comprises:

(i-a) identifying a group of one or more CHCs associated with lowest risk of VTE, wherein the identified group of CHCs associated with lowest risk of VTE comprises: a COC composition comprising nomegestrol acetate and estradiol or an ester thereof;

and wherein the selection in step (ii) is made from the group identified in step (i-a); optionally wherein in step (i-a) the CHCs identified as CHCs associated with lowest risk of VTE are the CHCs in the group comprising: a COC composition comprising nomegestrol acetate and estradiol or an ester thereof, and one or more of a COC composition comprising levonorgestrel, a COC composition comprising norgestimate, and a COC composition comprising norethisterone;

and wherein the selection in step (ii) is made from the group identified in step (i-a); and further optionally wherein in step (i-a) the CHCs identified as CHCs associated with lowest risk of VTE are the CHCs in the group comprising: a COC comprising nomegestrol acetate and estradiol or an ester thereof; a COC comprising levonorgestrel; a COC comprising norgestimate; and a COC comprising norethisterone.

3. The method of claim 1, wherein in step (i) the woman desirous of contraception is identified as suitable for receiving a CHC based on a determination of the VTE risk of the woman.

4. The method of claim 1, wherein prior to step (i), the method comprises the step of determining the VTE risk of the woman desirous of contraception.

5. The method of claim 1, wherein in step (i) the woman desirous of contraception is identified as suitable for receiving a CHC based on a determination of the unintended pregnancy risk of the woman; optionally wherein prior to step (i), the method comprises the step of determining the unintended pregnancy risk of the woman desirous of contraception.

6. The method of claim 1, wherein the woman desirous of contraception has not been administered a COC for at least 2 months; and/or wherein the woman desirous of contraception has not been administered a CHC for at least 2 months.

7. The method of claim 1, wherein the woman desirous of contraception has not previously been administered a COC; and/or wherein the woman desirous of contraception has not previously been administered a CHC.

8. The method of claim 1, wherein the woman desirous of contraception is at increased risk of unintended pregnancy.

9. The method of claim 1, wherein the woman desirous of contraception is 35 years of age or above.

10. The method of claim 1, wherein the woman desirous of contraception has a body mass index in excess of 30 $kg/m^2$ and/or has diabetes; and/or wherein the woman desirous of contraception has a body mass index of 30 $kg/m^2$ or less.

11. The method of claim 1, wherein the woman desirous of contraception does not have any condition selected from the group consisting of: systemic lupus erythematosus; hemolytic uremic syndrome; chronic inflammatory bowel disease; Crohn's disease; ulcerative colitis; and sickle cell disease; or wherein the woman desirous of contraception has a condition selected from the group consisting of: cancer; systemic lupus erythematosus; hemolytic uremic syndrome; chronic inflammatory bowel disease Crohn's disease; ulcerative colitis; and sickle cell disease.

12. The method of claim 1, wherein the nomegestrol acetate and estradiol or ester thereof are present in the COC composition in a weight ratio of approximately 1.67 to 1; and/or wherein the nomegestrol acetate is present in the COC in an amount ranging from about 1.5 mg to about 3.75 mg; and/or wherein the estradiol or ester thereof is present in the COC in an amount ranging from about 0.5 mg to about 3 mg.

13. The method of claim 1, wherein the estradiol is 17β-estradiol, optionally in hemihydrate form.

14. The method of claim 1, wherein the nomegestrol acetate is present in the COC in an amount of about 2.5 mg and the estradiol is present in the COC in an amount of about 1.5 mg.

15. The method of claim 1, wherein the COC composition is provided for administration daily for a period of 21 to 28 days or for a period of 24 consecutive days; and/or wherein the COC composition is provided as a pharmaceutical kit comprising a plurality of dosage units and optionally at least one placebo.

16. The method of claim 1, wherein the COC composition is in the form of a plain or a film-coated tablet, a sugar-coated tablet, a soft gelatin capsule, a wafer capsule, a pill, a cachet or a powder.

17. The method of claim 1, wherein the COC composition further comprises at least one excipient selected from the group consisting of: lactose monohydrate; microcrystalline cellulose (E460); crospovidone (E1201); talc (E553b); magnesium stearate (E572); and colloidal anhydrous silica; or any combination thereof; and/or wherein the COC composition comprises: 2.5 mg nomegestrol acetate; 1.5 mg 17β-estradiol; 57.7 mg lactose monohydrate; 14 mg microcrystalline cellulose; 2.4 mg crospovidone; 0.7 mg talc; 0.7 mg magnesium stearate; and 0.44 mg colloidal anhydrous silica.

18. The method of claim 1, wherein the woman desirous of contraception is less than 35 years of age.

19. The method according to claim 1, wherein the woman desirous of contraception has an increased genetic risk of VTE, and wherein the woman has at least one of the following: Factor V Leiden variant, Protein S deficiency and Protein C deficiency.

* * * * *